(12) United States Patent
Steiner et al.

(10) Patent No.: US 8,889,099 B2
(45) Date of Patent: *Nov. 18, 2014

(54) METHODS AND COMPOSITIONS FOR DELIVERING PEPTIDES

(71) Applicant: MannKind Corporation, Valencia, CA (US)

(72) Inventors: Solomon S. Steiner, Mount Kisco, NY (US); Rodney J. Woods, New Hampton, NY (US); Joseph W. Sulner, Paramus, NJ (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/754,698

(22) Filed: Jan. 30, 2013

(65) Prior Publication Data

US 2013/0143801 A1 Jun. 6, 2013

Related U.S. Application Data

(60) Continuation of application No. 12/985,197, filed on Jan. 5, 2011, now Pat. No. 8,389,470, which is a (Continued)

(51) Int. Cl.
*A61K 9/14* (2006.01)
*C07K 1/30* (2006.01)
(Continued)

(52) U.S. Cl.
CPC .............. *A61K 9/0075* (2013.01); *A61K 9/145* (2013.01); *Y10S 514/866* (2013.01);
(Continued)

(58) Field of Classification Search
USPC ............. 424/1.13, 489; 514/5.9, 6.8; 530/303
See application file for complete search history.

(56) References Cited

U.S. PATENT DOCUMENTS

| | | | |
|---|---|---|---|
| 3,906,950 | A | 9/1975 | Cocozza |
| 3,921,637 | A | 11/1975 | Bennie et al. |

(Continued)

FOREIGN PATENT DOCUMENTS

| | | |
|---|---|---|
| EP | 220958 | 5/1987 |
| EP | 257915 | 2/1988 |

(Continued)

OTHER PUBLICATIONS

Sajeesh et al. "Cyclodextrin-insulin complex encapsulated polymethacrylic acid based nanoparticles for oral insulin delivery," International Journal of Pharmaceutics, 2006, 325, pp. 147-154.*

(Continued)

*Primary Examiner* — Jane C Oswecki
(74) *Attorney, Agent, or Firm* — K&L Gates LLP; Louis C. Cullman; Hal Gibson

(57) ABSTRACT

Methods are provided for purifying peptides and proteins by incorporating the peptide or protein into a diketopiperazine or competitive complexing agent to facilitate removal one or more impurities, from the peptide or protein. Formulations and methods also are provided for the improved transport of active agents across biological membranes, resulting for example in a rapid increase in blood agent concentration. The formulations include microparticles formed of (i) the active agent, which may be charged or neutral, and (ii) a transport enhancer that masks the charge of the agent and/or that forms hydrogen bonds with the target biological membrane in order to facilitate transport. In one embodiment, insulin is administered via the pulmonary delivery of microparticles comprising fumaryl diketopiperazine and insulin in its biologically active form. This method of delivering insulin results in a rapid increase in blood insulin concentration that is comparable to the increase resulting from intravenous delivery.

14 Claims, 2 Drawing Sheets

Related U.S. Application Data continuation of application No. 12/635,380, filed on Dec. 10, 2009, now Pat. No. 7,943,178, which is a continuation of application No. 10/719,734, filed on Nov. 21, 2003, now Pat. No. 7,648,960, which is a continuation of application No. 10/224,761, filed on Aug. 20, 2002, now Pat. No. 6,652,885, which is a division of application No. 09/606,468, filed on Jun. 29, 2000, now Pat. No. 6,444,226.

(60) Provisional application No. 60/141,433, filed on Jun. 29, 1999.

(51) Int. Cl.
| | | |
|---|---|---|
| *A61K 9/00* | (2006.01) | |
| *A61K 9/16* | (2006.01) | |
| *C07K 14/605* | (2006.01) | |
| *A61K 38/05* | (2006.01) | |
| *A61K 38/28* | (2006.01) | |
| *C07D 241/08* | (2006.01) | |
| *C07K 14/62* | (2006.01) | |

(52) U.S. Cl.
CPC . *C07K 1/30* (2013.01); *A61K 38/28* (2013.01); *A61K 9/1676* (2013.01); *A61K 9/1617* (2013.01); *C07K 14/605* (2013.01); *C07K 14/62* (2013.01); *C07D 241/08* (2013.01)
USPC ............ 424/1.13; 424/489; 514/5.9; 514/6.8; 514/255.02; 530/303; 544/385; 514/866

(56) References Cited

U.S. PATENT DOCUMENTS

| | | | |
|---|---|---|---|
| 4,272,398 A | | 6/1981 | Jaffe |
| 4,356,167 A | | 10/1982 | Kelly |
| 4,483,922 A | | 11/1984 | Carpenter |
| 4,581,020 A | | 4/1986 | Mittleman |
| 4,849,227 A | | 7/1989 | Cho |
| 4,861,627 A | | 8/1989 | Mathiowitz |
| 4,866,051 A | | 9/1989 | Hunt et al. |
| 5,118,666 A | | 6/1992 | Habener |
| 5,120,712 A | | 6/1992 | Habener |
| 5,145,684 A | | 9/1992 | Liversidge et al. |
| 5,188,837 A | | 2/1993 | Domb |
| 5,260,306 A | | 11/1993 | Boardman et al. |
| 5,320,094 A | | 6/1994 | Laube et al. |
| 5,352,461 A | | 10/1994 | Feldstein et al. |
| 5,424,286 A | | 6/1995 | Eng |
| 5,458,135 A | | 10/1995 | Patton et al. |
| 5,492,112 A | | 2/1996 | Mecikalski et al. |
| 5,503,852 A | * | 4/1996 | Steiner et al. ................ 424/493 |
| 5,506,203 A | | 4/1996 | Backstrom et al. |
| 5,518,998 A | * | 5/1996 | Backstrom et al. .......... 424/489 |
| 5,547,929 A | | 8/1996 | Anderson, Jr. et al. |
| 5,574,008 A | | 11/1996 | Johnson et al. |
| 5,577,497 A | | 11/1996 | Mecikalski et al. |
| 5,631,224 A | | 5/1997 | Efendic et al. |
| 5,653,961 A | | 8/1997 | McNally et al. |
| 5,658,878 A | | 8/1997 | Backstrom et al. |
| 5,672,581 A | | 9/1997 | Rubsamen et al. |
| 5,693,338 A | | 12/1997 | Milstein |
| 5,740,794 A | | 4/1998 | Smith et al. |
| 5,747,445 A | | 5/1998 | Backstrom et al. |
| 5,785,049 A | | 7/1998 | Smith et al. |
| 5,874,064 A | | 2/1999 | Edwards et al. |
| 5,877,174 A | | 3/1999 | Ono et al. |
| 5,888,477 A | | 3/1999 | Gonda et al. |
| 5,901,703 A | | 5/1999 | Ohki et al. |
| 5,952,008 A | | 9/1999 | Backstrom et al. |
| 5,976,569 A | | 11/1999 | Milstein |
| 5,997,848 A | | 12/1999 | Patton et al. |
| 6,006,753 A | | 12/1999 | Efendic |
| 6,063,910 A | | 5/2000 | Debenedetti et al. |
| 6,071,497 A | * | 6/2000 | Steiner et al. .................. 424/45 |
| 6,132,766 A | | 10/2000 | Sankaram et al. |
| 6,153,613 A | | 11/2000 | Ono et al. |
| 6,187,291 B1 | | 2/2001 | Weinstein et al. |
| 6,191,102 B1 | | 2/2001 | DiMarchi et al. |
| 6,277,819 B1 | | 8/2001 | Efendic |
| 6,331,318 B1 | | 12/2001 | Milstein |
| 6,335,316 B1 | | 1/2002 | Hughes et al. |
| 6,348,447 B1 | | 2/2002 | Hellstrom et al. |
| 6,358,924 B1 | | 3/2002 | Hoffmann |
| 6,380,357 B2 | | 4/2002 | Hermeling et al. |
| 6,388,053 B1 | | 5/2002 | Galloway |
| 6,395,774 B1 | | 5/2002 | Milstein |
| 6,410,513 B1 | | 6/2002 | Galloway et al. |
| 6,428,771 B1 | * | 8/2002 | Steiner et al. .................. 424/45 |
| 6,440,463 B1 | | 8/2002 | Feldstein et al. |
| 6,444,226 B1 | * | 9/2002 | Steiner et al. ................ 424/489 |
| 6,447,751 B1 | | 9/2002 | Weinstein et al. |
| 6,555,521 B2 | | 4/2003 | Hermeling et al. |
| 6,583,111 B1 | | 6/2003 | DiMarchi et al. |
| 6,652,838 B2 | | 11/2003 | Weinstein et al. |
| 6,652,885 B2 | * | 11/2003 | Steiner et al. ................ 424/489 |
| 6,660,716 B1 | | 12/2003 | Yakubu-Madus et al. |
| 6,720,407 B1 | | 4/2004 | Hughes et al. |
| 6,747,006 B2 | | 6/2004 | Efendic |
| 6,923,175 B2 | | 8/2005 | Poole et al. |
| 6,989,155 B1 | | 1/2006 | Ganderton |
| 7,022,674 B2 | | 4/2006 | DeFelippis et al. |
| 7,084,243 B2 | | 8/2006 | Glaesner et al. |
| 7,101,843 B2 | | 9/2006 | Glaesner et al. |
| 7,144,863 B2 | | 12/2006 | DeFelippis et al. |
| 7,179,788 B2 | | 2/2007 | DeFelippis et al. |
| 7,211,557 B2 | | 5/2007 | DiMachi et al. |
| 7,223,728 B2 | | 5/2007 | Yakubu-Madus et al. |
| 7,232,897 B2 | | 6/2007 | Hotamisligil et al. |
| 7,238,663 B2 | | 7/2007 | DeFelippis et al. |
| 7,259,233 B2 | | 8/2007 | Dodd et al. |
| 7,278,419 B2 | | 10/2007 | Gonda et al. |
| 7,279,457 B2 | | 10/2007 | Pohl et al. |
| 7,305,986 B1 | | 12/2007 | Steiner et al. |
| 7,314,859 B2 | | 1/2008 | Green et al. |
| 7,464,706 B2 | | 12/2008 | Steiner et al. |
| 7,625,865 B2 | | 12/2009 | Colombo et al. |
| 7,648,960 B2 | * | 1/2010 | Steiner et al. ................. 514/1.1 |
| 7,943,178 B2 | | 5/2011 | Steiner et al. |
| 7,943,572 B2 | * | 5/2011 | Cheatham et al. ............. 514/5.9 |
| 8,119,593 B2 | * | 2/2012 | Richardson et al. ........... 514/5.9 |
| 8,389,470 B2 | * | 3/2013 | Steiner et al. .................. 514/5.9 |
| 8,394,414 B2 | * | 3/2013 | Steiner et al. ................. 424/493 |
| 2002/0052381 A1 | | 5/2002 | Bar-Or et al. |
| 2002/0065239 A1 | | 5/2002 | Caplan et al. |
| 2003/0017211 A1 | | 1/2003 | Steiner |
| 2004/0038865 A1 | | 2/2004 | Gelber et al. |
| 2004/0053819 A1 | | 3/2004 | Dodd |
| 2004/0062722 A1 | | 4/2004 | Gonda et al. |
| 2004/0096403 A1 | | 5/2004 | Steiner |
| 2004/0121964 A1 | | 6/2004 | Madar et al. |
| 2004/0182387 A1 | | 9/2004 | Steiner et al. |
| 2005/0043228 A1 | | 2/2005 | DeFelippis et al. |
| 2005/0153874 A1 | | 7/2005 | Cheatham et al. |
| 2006/0040953 A1 | | 2/2006 | Leone-Bay et al. |
| 2006/0041133 A1 | | 2/2006 | Stevenson et al. |
| 2006/0099269 A1 | | 5/2006 | Cheatham et al. |
| 2006/0120969 A1 | | 6/2006 | Nilsson et al. |
| 2006/0153778 A1 | | 7/2006 | Gelber et al. |
| 2006/0239934 A1 | | 10/2006 | Cheatham et al. |
| 2007/0020191 A1 | * | 1/2007 | Boss et al. ....................... 424/45 |
| 2007/0027063 A1 | | 2/2007 | Boss et al. |
| 2007/0059373 A1 | | 3/2007 | Oberg |
| 2007/0059374 A1 | | 3/2007 | Hokenson et al. |
| 2007/0196503 A1 | | 8/2007 | Wilson et al. |
| 2007/0207958 A1 | | 9/2007 | Bridon et al. |
| 2007/0240708 A1 | | 10/2007 | Schuckmann |
| 2008/0260838 A1 | | 10/2008 | Hokenson et al. |
| 2008/0260840 A1 | | 10/2008 | Alessi |
| 2009/0110647 A1 | | 4/2009 | Richardson |
| 2009/0111749 A1 | | 4/2009 | Richardson et al. |
| 2009/0258818 A1 | | 10/2009 | Surolia et al. |
| 2009/0308390 A1 | | 12/2009 | Smutney et al. |

| | | | |
|---|---|---|---|
| 2010/0086609 | A1 | 4/2010 | Steiner et al. |
| 2010/0113363 | A1 | 5/2010 | Holst et al. |
| 2011/0183901 | A1 | 7/2011 | Cheatham |
| 2012/0040899 | A1 | 2/2012 | Costello |
| 2012/0071510 | A1 | 3/2012 | Leone-Bay |
| 2012/0094905 | A1 | 4/2012 | Costello |
| 2012/0115777 | A1 | 5/2012 | Richardson |
| 2013/0125886 | A1 | 5/2013 | Richardson |

FOREIGN PATENT DOCUMENTS

| | | |
|---|---|---|
| EP | 1364967 | 11/2003 |
| EP | 1598066 | 11/2005 |
| EP | 2060268 | 5/2006 |
| GB | 2240337 | 7/1991 |
| JP | 363020301 | 1/1988 |
| JP | 2-149545 | 2/1992 |
| JP | 09-208485 | 8/1997 |
| JP | 2003-503420 | 1/2003 |
| WO | 91/04011 | 4/1991 |
| WO | 92/08509 | 5/1992 |
| WO | 93/02712 | 2/1993 |
| WO | 93/18754 | 9/1993 |
| WO | 94/08552 | 4/1994 |
| WO | 95/00127 | 1/1995 |
| WO | 96/36314 | 11/1996 |
| WO | 97/46206 | 12/1997 |
| WO | 99/52506 | 10/1999 |
| WO | 01/00654 | 1/2001 |
| WO | 02/098348 | 12/2002 |
| WO | 2004/103304 A2 | 12/2004 |
| WO | 2005/067964 | 7/2005 |
| WO | 2006/023943 | 3/2006 |
| WO | 2007/030706 | 3/2007 |
| WO | 2007/033316 | 3/2007 |
| WO | 2007/100535 | 9/2007 |
| WO | 2007/121411 | 10/2007 |
| WO | 2009/055742 | 4/2009 |
| WO | 2011/163272 | 12/2011 |

OTHER PUBLICATIONS

Angelo et al., Technosphere Insulin: Defining the Role of Technosphere Particles at the Cellular Level. J. Diabetes Sci. Technol., vol. 3, Issue 3, pp. 545-554 (2009).
Montrose-Rafizadeh et al., Diabetes, 45(Suppl. 2):152A, 1996.
Narayan et al. "Impact of recent increase in incidence on future diabetes burden." Diabetes Care 29:2114, 2006.
Naslund et al. "GLP-1 slows solid gastric emptying and inhibits insulin, glucagon, and PYY release in humans." Am J Physiol (Regulatory Integrative Comp Physiol 46):R910, 1999.
Naslund et al. "Prandial subcutaneous injections of glucagon-like petide-1 cause weight loss in obese human subjects." Br J Nutrition 91:439, 2004.
Nathan et al. "Intensive diabetes treatment and cardiovascular disease in patients with Type 1 diabetes." New Eng. J. Med. 353:2643-2653, 2005.
Nathan et al. "Management of hyperglycemia in Type 2 diabetes: a consensus algorithm for the initiation and adjustment of therapy." Diabetes Care 29:1963, 2006.
Nathan et al. "Management of hyperglycemia in Type 2 diabetes: a consensus algorithm for the initiation and adjustment of therapy." Diabetes Care 31:173, 2008.
Nathan et al. "Management of hyperglycemia in Type 2 diabetes: a consensus algorithm for the initiation and adjustment of therapy." Diabetes Care 32:193, 2009.
Nauck "Is glucagon-like peptide 1 an incretin hormone?" Diabetologia 42:373, 1999.
Nauck et al. "Glucagon-like peptide 1 inhibition of gastric emptying outweighs its insulinotropic effects in healthy humans." Am J Physiol 273 (Endocrinol Metabl 36):E981, 1997.
Nauck et al. "Reduced incretin effect in type 2 (non-insulin-dependent) diabetes." Diabetologia 29:46, 1986.
Nauck et al., Effects of glucagon-like peptide 1 on counterregulatory hormone responses, cognitive functions, and insulin secretion during hyperinsulinemic, stepped hypoglycemic clamp experiments in healthy volunteers. J Clin Endocrinol Metab., 87:1239-1246, 2002.
Nauck et al., Effects of subcutaneous glucagon-like peptide 1 (GLP-1 [7-36 amide]) in patients with NIDDM. Diabetologia, 39:1546-1553, 1996.
Nauck et al., Normalization of fasting hyperglycemia by exogenous GLP-1 (7-36 amide) in type 2 diabetic patients. Diabetologia, 36:741-744, 1993.
Nystrom et al. "Effects of glucagon-like peptide-1 on endothelial function in type 2 diabetic patients with stable coronary artery disease." Am J Physiol Endocrinol Metabl 287:E1209, 2004.
Office Action issued in connection with Russian Application No. 2010120666 mailed on Apr. 27, 2012.
Okumura et al., Intratracheal delivery of insulin: absorption from solution and aerosol by rat lung. Int. J. Pharmaceuticals 88: 63-73 (1992).Okumura et al., Intratracheal delivery of insulin: absorption from solution and aerosol by rat lung. Int. J. Pharmaceuticals 88: 63-73 (1992).
Oshima et al. "Comparison of half-disappearance times, distribution volumes and metabolic clearance rates of exogenous glucagon-like peptide 1 and glucagon in rats." Regulatory Peptides 21:85, 1988.
Owens et al. "Inhaled human insulin." Nature Reviews, Drug Discovery, vol. 5, No. 5, pp. 371-372, May 2006.
Ozyazgan et al. "Effect of glucagon-like peptide-1)7-36) and exendin-4 on the vascular reactivity in streptozotocin/nicotinamide-induced diabetic rats." Pharmacology 74:119, 2005.
Patton "Mechanisms of macromolecule absorption by the lungs." Advanced Drug Delivery Reviews 19:3, 1996.
Patton "Unlocking the opportunity of tight glycaemic control. Innovative delivery of insulin via the lung." Diabetes Obesity and Metabolism 7:S5, 2005.
Patton & Platz, Routes of Delivery: Case studies: pulmonary delivery of peptides and proteins for systemic action. Adv. Drug. Del. Rev. 8: 179-196 (1992).
Patton et al. "The lungs as a portal of entry for systemic drug delivery." Proc Am Thorac Soc 1:338, 2004.
Perera et al., Absorption and Metabolic Effect of Inhaled Insulin. Diabetes Care, vol. 25, No. 12, Dec. 2002, p. 2276-2281.
Pfeiffer Ma et al. Insulin secretion in diabetes mellitus. Am J Med 70:579-88, 1981.
Pfutzner et al "Technosphere/Insulin—A New Approach for Effective Delivery of Human Insulin Via the Pulmonary Route." Dibetes Technology & Therapeutics, vol. 4, No. 5, 2002, pp. 589-594.
Polonsky et al. Abnormal patterns of insulin secretion in non-insulin-dependent diabetes mellitus. N Eng J Med 318:1231-39, 1988.
Quattrin et al., Efficacy and Safety of Inhaled Insulin (Exubera) Compared with Subcutaneous Insuling Therapy in Patients with Type 1 Diabetes. Diabetes Care, vol. 27, No. 11, Nov. 2004, p. 2622-2627.
Quddusi et al. "Differential effects of acute and extended infusions of glucagon-like peptide-1 on first- and second-phase insulin secretion in diabetic and nondiabetic humans." Diabetes Care 26:791, 2003.
Rachman et al. "Normalization of insulin responses to glucose by overnight infusion of glucagon-like peptide 1 (7-36) amide in patients with NIDDM." Diabetes 45:1524, 1996.
Raskin et al. "Continuous subcutaneous insulin infusion and multiple daily injection therapy are equally effective in type 2 diabetes." Diabetes Care, vol. 26, No. 9, pp. 2598-2603, Sep. 2003.
Raufman et al., J. Biol. Chem. 266:2897-902, 1991.
Raufman et al., J. Biol. Chem. 267:21432-37, 1992.
Raun et al. "Liraglutide, a long-acting glucagon-like peptide-1 analog, reduces body weight and food intake in obese candy-fed rats, where as a dipeptidyl peptidase-IV inhibitor, vildagliptin, does not." Diabetes 56:8, 2007.
Rave et al. "Coverage of Postprandial Blood Glucose Excursions with Inhaled Technosphere Insulin in Comparison to Subcutaneously Injected Regular Human Insulin in Subjects with Type 2 Diabetes." Diabetes Care, vol. 30, No. 9, pp. 2307-2308, Sep. 2007.
Rave et al. "Inhaled Technosphere Insulin in Comparison to Subcutaneous Regular Human Insulin: Time Action Profile and Variability in Subjects with Type 2 Diabetes." Journal of Diabetes Science and Technology, vol. 2, Issue 2, pp. 205-212, Mar. 2008.

(56) References Cited

OTHER PUBLICATIONS

Rave et al. "Time-action profile of inhaled insulin in comparison with subcutaneously injected insulin lispro and regular human insulin." Diabetes Care 28:1077, 2005.
Raz I et al. "Pharmacodynamics and pharmacokinetics of dose ranging effects of Oralin versus s.c. regular insulin in Type 1 diabetic patients." Fourth Annual Diabetes Technology Meeting, Philadelphia, PA, 2004.
Razavi et al. "TRPVI+ sensory neurons control beta cell stress and islet inflammation in autoimmune disease." Cell 127:1123, 2006.
Richardson et al. "Technosphere Insulin Technology." Diabetes Technology & Therapeutics, vol. 9, Supplement 1, pp. S-65, 2007.
Richter et al. "Characterization of glucagon-like peptide-1(7-36)amide receptors of rat membranes by covalent cross-linking." FEBS Letters 280:247, 1991.
Richter et al. "Characterization of receptors for glucagon-like peptide-1 (7-36)amide on rat lung membranes." FEBS Letters 267:78, 1990.
Riddle et al. "Emerging therapies mimicking the effects of amylin and glucagon-like peptide 1." Diabetes Care 29:435, 2006.
Ritzel et al. "Pharmacokinetic, insulinotropic, and glucagonostatic properties of GLP-1 (7-36 amide) after subcutaneous injection in healthy volunteers. Dose-response-relationships." Diabetologia 38:720, 1995.
Rosenstock "Dual therapy with inhaled human insulin (Exubera(R)) as add-on to metformin (with stopping sulfonurea) is better than triple therapy with rosiglitazone add-on to combination metformin and sulfonurea in poorly controlled Type 2 diabetes." Diabetes 57:supplement 1:A557, Abstract 2018-PO, 2008.
Rosenstock et al. "Efficacy and Safety of Technosphere Inhaled Insulin Compared With Technosphere Powder Placebo in Insulin-Naive Type 2 Diabetes Suboptimally Controlled with Oral Agents." Diabetes Care, vol. 31, No. 11, pp. 2177-2182, Aug. 2008.
Rosenstock et al. "Inhaled insulin improves glycemic control when substituted for or added to oral combination therapy in Type 2 diabetes." Ann Intern Med 143:549-558, 2005.
Sajeesh et al., Cyclodextrin-insulin complex encapsulated polymethacrylic acid based nanoparticles for oral insulin delivery. International Journal of Pharmaceuticals, 2006, 325, pp. 147-154.
Kenny et al. "Dipeptidyl peptidase IV, a kidney brush-border serin peptidase." Biochem J. 155:169, 1976.
Kieffer et al. "The glucagon-like peptides." Endocrine Reviews 20:876, 1999.
Kim et al. "Development and characterization of a glucagon-like peptide 1-albumin conjugate. The ability to activate the glucagon-like peptide 1 receptor in vivo." Diabetes 52:751, 2003.
Kinzig et al. "The diverse roles of specific GLP-1 receptors in the control of food intake and the response to visceral illness." J Neurosci 22:10470, 2002.
Kirk et al. "Disparities in HbA1c levels between african-american and non-hispanic white adults with diabetes." Diabetes Care 29:2130, 2006.
Knop et al. "No hypoglycemia after subcutaneous administration of glucagon-like peptide-1 in lean type 2 diabetic patients and in patients with diabetes secondary to chronic pancreatitis." Diabetes Care 26:2581, 2003.
Knop et al. "Reduced incretin effect in type 2 diabetes. Cause or consequence of the diabetic state?" Diabetes 56:1951, 2007.
Kohler D et al. Non-radioactive approach for measuring lung permeability: inhalation of insulin. Atemw Lungenkrkh 13:230-232, 1987. (Original German and English translation attached).
Komatsu et al. "Glucagonostatic and insulinotropic action of glucagon-like peptide-1 (7-36)-amide." Diabetes 38:902, 1989.
Kreymann et al. "Glucagon-like peptide-1 7-36: a physiological incretin in man." The Lancet, Dec. 5, 1987, p. 1300.
Kwon et al. "Signaling elements involved in the metabolic regulation of mTOR by nutrients, incretins, and growth factors in islets." Diabetes 53:S225, 2004.

Lankat-Buttgereit et al. "Molecular cloning of a cDNA encoding for the GLP-1 receptor expressed in rat lung." Exp Clin Endocrinol 102:241, 1994.
Lebovitz "Therapeutic options in development for management of diabetes: pharmacologic agents and new technologies." Endocr Pract 12:142, 2006.
Lee et al. "Synthesis, characterization and pharmacokinetic studies of PEGylated glucagon-like peptide-1." Bioconjugate Chem 16:377, 2005.
Leone-Bay et al. "Evaluation of novel particles as an inhalation system for GLP-1." Diabetes, Obesity and Metabolism. 11:1050-1059, 2009.
Li et al. "GLP-1; a novel zinc finger protein required in somatic cells of the gonad for germ cell development." Dev Biol 301:106, 2007.
Luque et al. "Glucagon-like peptide-1 (GLP-1) and glucose metabolism in human myocytes." J. Endocrinol 173:465, 2002.
M. Combettes and Kargar, C, Newly Approved and Promising Antidiabetic Agents. Therapie, Jul.-Aug. 2007: 62 (4): 293-310.
Malhotra et al., Regulatory Peptides, 41:149-56, 1992.
MannKind Corporation "Postprandial hyperglycemia: clinical significance, pathogenesis and treatment." MannKind Corporation Monograph. 2009.
Marshall "Preventing and detecting complications of diabetes." BMJ 333:455, 2006.
Matsui et al. "Hyperplasia of type II pheumocytes in pulmonary lymphangioleiomyomatosis. Immunohistochemical and electron microscope study." Arch Pathol Lab Med 124:1642, 2000.
Matthews et al. "Homeostasis model assessment: insulin resistance and beta-cell function from fasting plasma glucose and insulin concentrations in man." Diabetologia. Jul. 1985; 28(7):412-9.
McElduff et al. "Influence of acute upper respiratory tract infection on the absorption of inhaled insulin using the AERx(R) insulin diabetes management system." Br J Clin Pharmacol 59:546, 2005.
Meier et al. "Absence of a memory effect for the insulinotropic action of glucagon-like peptide-1 (GLP-1) in healthy volunteers." Horm Metab Res 35:551, 2003.
Meier et al. "Secretion, degradation, and elimination of glucagon-like peptide-1 and gastric inhibitor polypeptide in patients with chronic renal insufficiency and healthy control subjects." Diabetes 53:654, 2004.
Meier et al. "The glucagon-like peptide-1 metabolite GLP-1-(9-36) amide reduces postprandial glycemia independently of gastric emptying and insulin secretion in humans." Am J Physiol Endocrinol Metab 290:E1118, 2006.
Mentlein et al., Dipeptidyl peptidase IV hydrolyses gastric inhibitory polypeptide, glucagon-like peptide-1 (7-36) amide, peptide histidine methionine and is responsible for their degradation in human serum. Eur J Biochem., 214:829-835, 1993.
Merck Manual 17th, Japanese Edition, NIKKEI BP Corp., 1999, p. 167-179.
Mitchell et al. "Intranasal Insulin: PK Profile Designed Specifically for Prandial Treatment of Type 2 Diabetes." Drug Development Research 69(3):143-152 (2008).
Monnier et al. "Activation of oxidative stress by acute glucose fluctuations compared with sustained chronic hyperglycemia in patients with type 2 diabetes." JAMA 295:1681, 2006.
Johnson et al., Peptide turn mimetics, Biotechnology and Pharmacy, Ed JM Pezzuto et al., Chapman & Hall, New York, pp. 366-378 (1993).
Okumura et al., Intratracheal delivery of insulin: absorption from solution and aerosol by rat lung. Int. J. Pharmaceuticals 88: 63-73 (1992).
ACTOS Product Insert. Aug. 2008.
Ahren "GLP-1 and extra-islet effects." Horm Med Res 36:842, 2004.
Ahren et al. "Characterization of GLP-1 effects on b-cell function after meal ingestion in humans." Diabetes Care 26:2860, 2003.
Alabraba et al. Diabetes Technology & Therapeutics. Jul. 2009, 11(7): 427-430.
American Diabetes Association. "Standards of medical care in diabetes—2009." Diabetes Care. Jan. 2009; 32 Suppl 1:S13-61.
AVANDIA Product Insert, Oct. 2008.
Baggio et al. "A recombinant human glucagon-like peptide (GLP)-1-albumin protein (Albugon) mimics peptidergic activation of GLP-1

(56) References Cited

OTHER PUBLICATIONS receptor-dependent pathways coupled with satiety, gastrointestinal motility, and glucose homeostatsis." Diabetes 53:2492, 2004.
Baggio et al. "Glucagon-like peptide-1, but not glucose-dependent insulinotropic peptide, regulates fasting glycemia and noneneteral glucose clearance in mice." Endocrinology 141:3703, 2000.
Baggio et al. "Harnessing the therapeutic potential of glucagon-like peptide-1." Treat Endocrinol 1:117, 2002.
Balkan et al. "Portal GLP-1 administration in rats augments the insulin response to glucose via neuronal mechanisms." Am J. Physiol Regulatory Integrative Comp Physiol 279:R1449, 2000.
Barnett et al. "An open, randomized, parallel-group study to compare the efficacy and safety profile of inhaled human insulin (Exubera) with Glibenclamide as adjunctive therapy in patients with Type 2 diabetes poorly controlled on Metformin." Diabetes Care 29:1818-1825, 2006.
Barnett et al. "An open, randomized, parallel-group study to compare the efficacy and safety profile of inhaled human insulin (Exubera) with metformin as adjuvant therapy in patients with Type 2 diabetes poorly controlled on a sulfonylurea." Diabetes Care 29:1282, 2006.
Barragan et al. "Changes in arterial blood pressure and heart rate induced by glucagon-like peptide-1-(7-36) amide in rats." Am J. Physiol 266 (Endocrinol Metab 29):E459, 1994.
Behme et al. "Glucagon-like peptide-1 improved glycemic control in type 1 diabetes." BMC Endocrine Disorders 3:3, 2003.
Bellary et al. "Inhaled insulin:new technology, new possibilities." Int J Clin Pract 60:728, 2006.
Benita, Charaterization of Drug-Loaded Poly(d,l-lactide) Microspheres. J. Pharm. Sci., 73: 1721-1724 (1984).
Benito et al. "Glucagon-like peptide-1-(7-36) amide increases pulmonary surfactant secretion through a cyclic adenosine 3',5'-monophosphate-dependent protein kinase mechanism in rat type II pneumocytes." Endocrinology 139:2363, 1998.
Bensch et al., Absorption of intact protein molecules across the pulmonary air-tissue barrier, Science 156: 1204-1206 (1967).
Biodel's Intellecutal Property position strengthened for ultra-rapid-acting insulin programs by notice of intent to grant from European Patent Office. Newswire Fee, published May 2, 2012.
Blazquez et al. "Glucagon-like peptide-1 (7-36) amide as a novel neuropeptide." Mol Neurobio 18:157, 1998.
Bloomgarden "Gut-derived incretin hormones and new therapeutic approaches." Diabetes Care 27:2554, 2004.
Bojanowska "Physiology and pathophysiology of glucagon-like peptide-1 (GLP-1): the role of GLP-1 in the pathogenesis of diabetes mellitus, obesity and stress." Med Sci Monit 11:RA271, 2005.
Boss et al. "Prandial Insulin: Is Inhaled Enough?" Drug Development Research 69(3):138-142 (2008).
Bray "Exanatide" Am J Health-Sys Pharm 63:411, 2006.
Brownlee et al. "Glycemic variability: a hemoglobin A1c-independent risk factor for diabetic complications." JAMA 295:1707, 2006.
Bullock et al. "Tissue distribution of messenger ribonucleic acid encoding the rat glucagon-like peptide-1 receptor." Endocrinology 137:2968, 1996.
Burcelin et al. "Encapsulated, genetically engineered cells, secreting glucagon-like peptide-1 for the treatment of non-insulin-dependent diabetes mellitus." Ann N Y Acad Sci. Jun. 18, 1999;875:277-85.
Campos et al. "Divergent tissue-specific and developmental expression of receptors for glucagon and glucagon0like peptide-1 in the mouse." Endocrinology 134:2156, 1994.
Cefalu et al., Concept, strategies and feasibility of noinvasive insulin delivery. Diabetes Care 27: 239-246, 2004.
Cefalu et al., Inhaled human insulin treatment in patients with type 2 diabetes mellitus. Ann. Int. Med., 2001, 134, 203-7.
Ceglia et al. "Meta-analysis: efficacy and safety of inhaled insulin therapy in adults with diabetes mellitus." Ann Intern Med 145:665, 2006.
Cerasi et al., Decreased sensitivity of the pancreatic beta cells to glucose in prediabetic and diabetic subjects. A glucose dose-response study. Diabetes 21 (4): 224-34, 1974.

Cernea et al. "Dose-response relationship of oral insulin spray in healthy subjects." Diabetes Care, vol. 28, No. 6, pp. 1353-1357, Jun. 2005.
Cernea et al. "Noninjectable Methods of Insulin Administration." Drugs of Today 2006, 42 (6): 405-424.
Cheatham et al. "Desirable dynamics & performance of inhaled insulin compared to subcutaneous insulin given at mealtime in type 2 diabetes: A report from the technosphere/insulin study group." pp. 234-235, 2004.
Cheatham et al., Desirable dynamics and performance of inhaled insulin compared to subcutaneous insulin given at mealtime in type 2 diabetes: A report from the technosphere/insulin study group. Diabetes Technology and Therapeutics, vol. 6, p. 234, 2004.
Chelikani et al., Intravenous infusion of glucagon-like peptide-1 potently inhibits food intake, sham feeding, and gastric emptying in rats. Am J Physiol. Regul. Integr. Comp. Physiol., 288(6):R1695-706, 2005.
Clee et al. Nature Genetics 38:688-693, 2006.
Cobble "Initiating and Intensifying Insulin Therapy for Type 2 Diabetes: Why, When, and How." Am J Ther. Jan. 8, 2009.
Coffey et al. "Valuing heath-related quality of life in diabetes." Diabetes Care 25:2238, 2002.
Cruetzfeldt et al. "Glucagonostatic actions and reduction of fasting hyerglycemia by exogenous glucagon-like peptide i(7-36) amide in type 1 diabetic patients." Diabetes Care 19:580, 1996.
D'Alessio et al., J. Clin. Invest., 97:133-38, 1996.
Davis "Postprandial Physiology and the Pathogenesis of Type 2 Diabetes Mellitus." Insulin, vol. 3, Apr. 1, 2008, pp. 132-140.
De Heer et al. "Sulfonylurea compounds uncouple the glucose dependence of the insulinotropic effect of glucagon-like peptide-1." Diabetes 56:438, 2007.
Deacon "Therapeutic strategies based on glucagon-like peptide 1." Diabetes. Sep;53(9):2181-9, 2004.
Deacon et al., "Glucagon-like peptide 1 undergoes differential tissue-specific metabolism in the anesthetized pig", Am. J. Physiol. 271 (Endocrino. Metab. 34): E458-E464, 1996.
Decode study group. "Glucose tolerance and mortality: comparison of WHO and American Diabetes Association diagnostic criteria." Lancet. Aug. 21, 1999;354(9179):617-21.
Delgado-Aros et al. "Effect of GLP-1 on gastric volume, emptying, maximum volume ingested and postprandial symptoms in humans." Am J Physiol Gastrointest Liver Physiol 282:G424, 2002.
Doyle et al. "Glucagon-like peptide-1." Recent Prog Norm Res. 2001;56:377-99.
Drucker "Development of glucagon-like peptide-1-based pharmaceuticals as therapeutic agents for the treatment of diabetes." Curr Pharma Design 7:1399, 2001.
Joy et al. "Incretin mimetics as emerging treatments for type 2 diabetes." Annal Pharmacother 39:110, 2005.
Juntti-Berggren et al. "The antidiabetogenic effect of GLP-1 is maintained during a 7-day treatment period and improves diabetic dyslipoproteinemia in NIDDM patients." Diabetes Care 19:1200, 1996.
Kanse et al. "Identification and characterization of glucagon-like peptide-1 7-36 amide-binding sites in the rat brain and lung." FEBS Letters 241:209, 1988.
Kapitza et al. "Impact of particle size and aerosolization time on the metabolic effect of an inhaled insulin aerosol." Diabetes Tech Ther 6:119, 2004.
Katchalski, Synthesis of Lysine Anhydride. J. Amer. Chem. Soc. 68: 879-880 (1946).
Katz et al. "Quantitative insulin sensitivity check index: a simple, accurate method for assessing insulin sensitivity in humans." J. Clin. Endocrinol. Metab. 85:5402-2410, 2000.
Kaur et al. "A Delineation of Diketopiperazine Self-Assembly Processes: Understanding the Molecular Events Involved in Nε-(Fumaroyl)diketopiperazine of L-Lys (FDKP) Interactions." Molecular Pharmaceutics, vol. 5, No. 2, 294-315, 2008.
Kawai et al. "Evidence that glucagon stimulates insulin secretion through its own receptor in rats." Diabetologia 38:274, 1995.
Komada et al., Intratracheal delivery of peptide and protein agents: absorption from solution and dry powder by rat lung. J. Pharm. Sci. 83(6): 863-867 (1994).

(56) References Cited

OTHER PUBLICATIONS

Kopple et al. "A convenient synthesis of 2,5-piperazinediones." J Org Chem p. 962, 1967.
Kopple, A convenient synthesis of 2,5-piperazinediones. J. Org. Chem., 33(2): 862-864 (1968).
Leahy et al., Beta-cell dysfunction in type 2 diabetes mellitus. Curr. Opin. Endocrinol. Diabetes, 2: 300-306, 1995.
Lian et al., A self-complementary self-assembling microsphere system: application for intravenous delivery of the antiepileptic andneuroprotectant compound felbanate. J. Pharm Sci. 89: 867-875, 2000.
Lim, Microencapsulation of Living Cells and Tissues. J. Pharm. Sci., 70: 351-354 (1981).
Mathiowitz, Morphology of Polyanhydride Microsphere Delivery Systems, Scanning Microscopy, 4: 329-340 (1990).
Mathiowitz, Novel microcapsules for delivery systems. Reactive Polymers, 6: 275-283 (1987).
Mathiowitz, Polyanhydride microspheres as drug carriers I, hot-melt microencapsulation. J. Controlled Medicine, 5: 13-22 (1987).
Mathiowitz, Polyanhydride microspheres as drug carriers II, microencapsulation by solvent removal. J. Appl. Polymer Sci., 35: 755-774 (1988).
Mathiowitz, Polyanhydride microspheres IV, morphology and characterization systems made by spray drying. J. App. Polymer Sci., 45: 125-134 (1992).
Matsui et al. "Hyperplasia of type II pheumocytes in pulmonary lymphangioleiomyomatosis. Immunohistochemical and electron microscope study." Arch Pathol Lab Med 124:1642, 2000.
Matthews et al. "Homeostasis model assessment: insulin resistance and beta-cell function from fasting plasma glucose and insulin concentrations in man." Diabetologia. Jul. 1985;28(7):412-9.
Drucker et al., "The incretin system:glucagon-like peptide-1 receptor agonists and dipeptidyl peptidase-4 inhibitors in type 2 diabetes", www.thelancet.com, vol. 368, pp. 1696-1705, Nov. 11, 2006.
Edelman SV Type II diabetes mellitus. Adv Int Med 43:449-500, 1998.
Edwards et al. "Cardiovascular and pancreatic endocrine response to glucagon-like peptide-1(7-36) amide in the conscious calf." Exp Physiol 82:709, 1997.
Edwards et al. "Subcutaneous glucagon-like peptide-1(7-36) amide is insulinotropic and can cause hypoglycaemia in fasted healthy subjects." Clinical Science 96:719, 1998.
Ehlers et al. "Recombinant glucagon-like peptide-1 (7-36 amide) lowers fasting serum glucose in a broad spectrum of patients with type 2 diabetes." Horm Metab Res 35:611, 2003.
Eissele et al., Life Sci., 55:629-34, 1994.
Elliot et al., Parenteral absorption of insulin from the lung in diabetic children. Austr. Paediatr. J. 23: 293-297 (1987).
Elrick et al. "Plasma insulin response to oral and intravenous glucose administration." J Clin Endocr 24:1076, 1964.
Engwerda et al., Improved pharmackinetic and pharmacodynamic profile of rapid-acting insulin using needle-free jet injection technology. Diabetes Care, vol. 34, Aug. 2011, pp. 1804-1808.
EP Office Action, Application No. 10 005 945.0 mailed Dec. 28, 2011.
Farr, S.J. et al., Pulmonary insulin administration using the AERx®system:physiological and physiochemical factors influencing insulin effectiveness in healthy fasting subjects. Diabetes Tech. Ther. 2:185-197, 2000.
Fehmann et al. "Cell and molecular biology of the incretin hormones glucagon-like peptide-1 and glucose-dependent insulin releasing polypeptide." Endocrine Reviews 16:390, 1995.
Glucophage Product Insert. Jan. 2009.
Glucotrol Product Insert. Sep. 2006.
Goke et al., J. Biol. Chem. 268:19650-55, 1993.
Golpon et al. "Vasorelaxant effect of glucagon-like peptide-(7-36) amide and amylin on the pulmonary circulation of the rat." Regulatory Peptides 102:81, 2001.

Greene et al. "Effects of GLP-1 Technosphere(TM) powder: administered by pulmonary insufflation in male obese Zucker diabetic fat (ZDF) rats." Diabetes Technology Meeting, San Francisco, Oct. 2007.
Gupta, Contemporary Approaches in Aerosolized Drug Delivery to the Lung. J. Controlled Release, 17(2): 127-147 (1991).
Gutniak et al. "Antidiabetogenic action of glucagon-like peptide-1 related to administration relative to meal intake in subjects with type 2 diabetes." J Int Med 250:81, 2001.
Gutniak et al. "Antidiabetogenic effect of glucagon-like peptide-1 (7-36)amide in normal subjects nad patients with diabetes mellitus." NEJM 326:1316, 1992.
Gutniak et al. "GLP-1 tablet in type 2 diabetes in fasting and postprandial conditions." Diabetes Care 20:1874, 1997.
Gutniak et al. "Potential therapeutic levels of glucagon-like peptide I achieved in humans by a buccal tablet." Diabetes Care 19:843, 1996.
Gutniak et al. "Subcutaneious injection of the incretin hormone glucagon-like peptide 1 abolishes postprandial glycemia in NIDDM." Diabetes Care 17:1039, 1994.
Guyton et al., "Acute Control of Llocal Blood Flow", Textbook of Medical Physiology, Chapter 17, 10th Edition, W.B. Saunders Company, pp. 176-177, 2000.
Haak "New developments in the treatment of type 1 diabetes mellitus." Exp Clin Endocrinol Diabetes 107:Suppl 3: S108, 1999.
Halozyme Press Release. Jun. 6, 2009.
Hassan et al. "In vivo dynamic distribution of 131I-glucagon0like peptide-1 (7-36) amide in the rat studied by gamma camera." Nucl Med Biol 26:413, 1999.
Hausmann et al. "Inhaled insulin as adjunctive therapy in subjects with type 2 diabetes failing oral agents: a controlled proof of concept study." Diabetes Obesity and Metabolism 8:574, 2006.
Hausmann et al. "Inhaled insulin as adjunctive therapy in subjects with type 2 diabetes failing oral agents: a controlled proof-of-concept study." Diabetes Obesity Metab 8:574-580, 2006.
Hayasaka et al. "Proliferation of type II pneumocytes and alteration in their apical surface membrane antigenicity in pulmonary sarcoidosis." Chest 116:477, 1999.
Heine "Unlocking the opportunity of tight glycaemic control. Promise ahead: the role of inhaled insulin in clinical practice." Diabetes, Obesity and Metabolism 7:S19, 2005.
Heinemann "Variability of Insulin Absorption and Insulin Action." Diabetes Technology & Therapeutics, vol. 4, No. 5, pp. 673-682. 2002.
Heinemann et al. "Current status of the development of inhaled insulin." Br. J. Diabetes Vase. Dis. 4:295-301, 2004.
Heinemann et al. "Time-action profile of inhaled insulin." Diabetic Med 14:63, 1996.
Heise et al. "The effect of insulin antibodies on the metabolic action of inhaled and subcutaneous insulin." Diabetes Care 28:2161, 2005.
Heyder, Alveolar deposition of inhaled particles in humans. Am. Ind. Hyg. Assoc. J. 43(11): 864-866 (1982).
Hite et al. "Exhuberance over Exubera." Clin Diabetes 24(3):110-114, 2006.
Hollander et al., Efficacy and Safety of Inhaled Insulin (Exubera) Compared with Subcutaneous Insulin Therapy in Patients with Type 2 Diabetes. Diabetes Care, vol. 27, No. 10, Oct. 2004, p. 2356-2362.
Holst "Therapy of type 2 diabetes mellitus based on the actions of glucagon-like peptide-1." Diabetes Metab Res Rev 18:430, 2002.
Holst et al. "On the effects of glucagon-like peptide-1 on blood glucose regulation in normal and diabetic subjects." Ann N Y Aced Sci. Dec. 26, 1996;805:729-36.
Huda et al. "Gut peptides and the regulation of appetite." Obesity Reviews 7:163, 2006.
Hussain et al., State of insulin self-association does not affects its absorption from the pulmonary route. Eur. J. Pharm. Sciences 25: 289-298, 2005.
Imeryuz et al. "Glucagon-like peptide-1 inhibits gastric emptying via vagal afferent-mediated central mechanisms." Am J Physiol 273 (Gastrointest Liver Physiol 36):G920, 1997.
International Search Report for PCT/US2011/060057 mailed on Jan. 20, 2012.

(56) References Cited

OTHER PUBLICATIONS

Iwanij et al., Characterization of the Glucagon Receptor and its Functional Domains Using Monoclonal Antibodies. The Journal of Biological Chemistry, vol. 265, No. 34, pp. 21302-21308, 1990.
Japanese Office Action for related case 2008-504512 issued Sep. 15, 2011.
Johnson et al. "Peptide turn mimetics." in Biotechnology and Pharmacy, Ed JM Pezzuto et al. Chapman & Hall, New York, pp. 366.
Johnson et al: RyR2 and calpain-10 delineate a novel apoptosis pathway in pancreatic islets. J Biol Chem., 279 (23):24794-802, 2004.
Jones et al., An investigation of the pulmonary absorption of insulin in the rat. Third European Congress of Biopharmaceutics and Pharmacokinetics, (1987).
Joseph et al. "Oral delivery of glucagon-like peptide-1 in a modified polymer preparation normalizes basal glycaemia in diabetic db/db mice." Diabetologia 43:1319, 2000.
Sakr, A new approach for insulin delivery via the pulmonary route: design and pharmacokinetics in non-diabetic rabbits. International Journal of Pharmaceutics, 86: 1-7 (1992).
Salib, Utilization of sodium alginate in drug microencapsulation. Pharazeutische Industrie, 40(11a): 1230-1234 (1978).
Saraceni et al. "Effects of glucagon-like peptide-1 and long-acting analogues on cardiovascular and metabolic function." Drugs R D 8:145, 2007.
Savage et al., "Effects of peptide YY (PYY) on mouth to caecum intestinal transit time and on the rate of gastric emptying healthy volunteers", Gut, vol. 28, pp. 166-170, 1987.
Sawhney, Bioerodible hydrogels based on photopolymerized poly-(ethylene glycol)-co-poly(a-hydroxy acid) diacrylate macromers. Macromolecules, 26: 581-587 (1993).
Schaffer et al. "Assembly of high-affinity insulin receptor agonists and antagonists from peptide building blocks." PNAS 100:4435, 2003.
Schepp et al., Eur. J. Pharmacol., 69:183-91, 1994.
Scherbaum "Unlocking the opportunity of tight glycaemic control. Inhaled insulin: clinical efficacy." Diabetes Obesity and Metabolism 7:S9, 2005.
Schirra et al. "Gastric emptying and release of incretin hormones after glucose ingestion in humans." J Clin Invest 97:92, 1996.
Scrocchi et al. "Glucose intolerance but normal satiety in mice with a null mutation in the glucagon-like peptide 1 receptor gene." Nature Medicine 2:1254, 1996.
Shah et al. "Lack of suprression of glucagon contributes to postprandial hyperglycemia in subjects with type 2 diabetes mellitus." J Clin Indocrinol Metab 85:4053, 2000.
Shelly et al. "Polysorbate 80 hypersensitivity." The Lancet 345:1312, 1995.
Shojania et al. "Effect of quality improvement strategies for type 2 diabetes on glycemic control." JAMA 296:427, 2006.
Singh, et al., Regul. Pept. 53:47-59, 1994.
Skyler "Pulmonary Insulin Delivery—State of the Art 2007." Diabetes Tecnology & Therapeutics, vol. 9, Supplement 1, pp. S1-S3. 2007.
Smith et al. "New-onset diabetes and risk of all-cause and cardiovascular mortality." Diabetes Care 29:2012, 2006.
Stanley et al. "Gastrointestinal satiety signals III. Glucagon-like peptide 1, oxyntomodulin, peptide YY and pacretic peptide." Am J Physiol Gastrointest Liver Physiol 286:G693, 2004.
Steinberg et al. "A new approach to the safety assessment of pharmaceutical excipients." Reg Toxicol Pharmacol 24:149, 1996.
Steiner et al. "A novel glucagon delivery system for the management of hyperinsulinemia." Diabetes 49 Supplement, Abstract 1545-PO, 2000.
Steiner S et al. Technosphere(TM)/Insulin—proof of concept study with a new insulin formulation for pulmonary delivery. Exp Clin Endocrinol Diabetes 110:17-21, 2002.
Stowell et al. "Development of GLP-1 Technosphere(TM) powder: an inhaled GLP-1 product." Diabetes Technology Meeting, San Francisco, Oct. 2007.

Strack "Inhaled Human Insulin." Drugs of Today 2006, 42 (4): 207-221.
Sturis et al., British Journal of Pharmacology, 140,123 .132, 2003.
Tack Cees J. et al., Forced Titration to Different Doses of Technosphere Insulin Demonstrates Reduction in Postprandial Glucose Excursions and Hemoglobin A1c in Patients with Type 2 Diabetes. Journal of Diabetes Science and Technology, vol. 2, Issue 1, pp. 47-57, Jan. 2008.
Tang-Christensen et al. "Central administration of GLP-1-(7-36) amide inhibits food and water intake in rats." Am J Physiol 271 (Regulatory Integrative Comp Physiol 40):R848, 1996.
Teeter et al. "Dissociation of lung function changes with humoral immunity during inhaled human insulin therapy." Am J Resp Crit Care Med 173:1194, 2006.
Thorens "Expression cloning of the pancreatic b-cell receptor for the gluco-incretin hormone glucagon-like peptide-1." PNAS 89:8641, 1992.
Thorens et al. "Cloning and function expression of the human islet GLP-1 receptor: demonstration that exendin-4 is an agonist and exendin-(9-39) an antagonist of the receptor." Diabetes 42:1678, 1993.
Todd et al. "Glucagon-like peptide-1 (GLP-1: a trial of treatment in on-insulin-dependent diabetes mellitus." Eur J Clin Invest 27:533, 1997.
Todd et al. Subcutaneous glucagon-like peptide-1 improves postprandial glucaemic control over a 3-week period in patients with early type 2 diabetes. Clinical Science 95:325, 1998.
Toft-Nielson et al. "Determinants of the effectiveness of glucagon-like peptide-1 in type 2 diabetes." J Clin Endocrinol Metab 86:3853, 2001.
Toft-Nielson et al. "Exaggerated secretion of glucagon-like peptide-1 (GLP-1) could cause reactive hypoglcaemia." Diabetologia 41:1180, 1998.
Toft-Nielson et al. "The effect of glucagon-like peptide-1 (GLP-1) on glucose elimination in healthy subjects depends on the pancreatic glucoregulatory hormones." Diabetes 45:552, 1996.
Tornusciolo et al., Biotechniques 19(5):800-805, 1995. Simultaneous detection of TDT-mediated dUTP-biotin nick end-labeling (TUNEL)-positive cells and multiple immunohistochemical markers in single tissue sections.
US Office Action cited in U.S. Appl. No. 12/985,197 mailed on Jan. 20, 2012.
Vahl et al. "Effects of GLP-1-(7-36)NH2, GLP-1-(7-37), and GLP-1-(9-36)NH2 on intravenous glucose tolerance and glucose-induced insulin secretion in healthy humans." J Clin Endocrinol Metabol 88:1772, 2003.
Vara et al. "Glucagon-like peptide-1 (7-36) amide stimulates surfactant secretion in human type II pneumocytes." Am J Resp Crit Care Med 163:841, 2001.
Vella et al. "Effect of glucagon-like peptide 1(7-36) amide on glucose effectiveness and insulin action in people with type 2 diabetes." Diabetes 49:611, 2000.
Vella et al. "The gastrointestinal tract and glucose tolerance." Curr Opin Clin Nutr Metab Care 7:479, 2004.
Verdich et al., A meta-analysis of the effect of glucagon-like peptide-1 (7-36) amide on ad libitum energy intake in humans. J Clin Endocrinol Metab., 86:4382-4389, 2001.
Vilsboll et al. "Reduced postprandial concentrations of intact biologically active glucagon-like peptide-1 in type 2 . diabetic patients." Diabetes 50:609, 2001.
Vilsboll et al. "Similar elimination rates of glucagon-like peptide-1 in obese type 2 diabetic patients and healthy subjects." J Clin Endocrinol Metab 88:220, 2003.
Vilsboll et al., "Evaluation of β-Cell Secretary Capacity Using Glucagon-Like Peptide 1", Diabetes Care, vol. 23, No. 6, pp. 807-812, Jun. 2000.
Vilsboll et al., "Incretin secretion in Relation to Meal Size and Body Weight in Healthy Subjects and People with Type 1 and Type 2 diabetes Mellitus", The Journal of Clinical Endrocronology & Metabolism, vol. 88, No. 6, pp. 2706-2713, 2003.
Volund "Conversion of insulin units to SI units." American Journal of Clinical Nutrition, Nov. 1993, 58(5), pp. 714-715.

(56) References Cited

OTHER PUBLICATIONS

Wachters-Hagedoorn et al. "The rate of intestinal glucose absorption is correlated with plasma glucose-dependent insulinotropic polypeptide concentrations in healthy men." J Nutr 136:1511, 2006.
Wang et al., Glucagon-like peptide-1 regulates proliferation and apoptosis via activation of protein kinase B in pancreatic INS-1 beta cells. Diabetologia, 47:478-487, 2004.
Wang et al., J. Clin. Invest., 95:417-21, 1995.
Warren et al. "Postprandial versus preprandial dosing of biphasic insulin apart in elderly type 2 diabetes patients." Diabetes Research and Clinical Practive, vol. 66, pp. 23-29, 2004.
Wei et al. "Tissue-specific expression of the human receptor for glucagon-like peptide-1: brain and pancreatic forms have the same deduced amino acid sequence." FEBS Letters 358:219, 1995.
Weir et al. "Glucagonlike peptide 1 (7-37) actions on endocrine pancreas." Diabetes 38:338, 1989.
Wettergren et al. "Truncated GLP-1 (proglucagon 78-107-Amide) inhibits gastric and pancreatic functions in man." Digestive Diseases and Sciences 38:665, 1993.
Wigley et al., Insulin across respiratory mucosae by aerosol delivery. Diabetes 20(8): 552-556 (1971).
Willms et al. "Gastric emptying, glucose responses, and insulin secretion after a liquid test meal: effects of exogenous glucagon-like peptide-1 (GLP-1)-(7-36) amide in type 2 (noninsulin-dependent) diabetic patients." J. Clin Endocrinol Metab 81:327, 1996.
Wilson et al. "Technospheres(TM) for pulmonary and nasal applications." Respiratory Drug Delivery VIII, 2002, p. 545.
Witchert, Low molecular weight PLA: A suitable polymer for pulmonary administered microparticles. J. Microencapsulation, 10(2): 195-207 (1993).
Wong et al. "From cradle to grave: pancreatic b-cell mass and glucagon-like peptide-1." Minerva Endocrinologica 31:107, 2006.
Yoshida et al., Absorption of insulin delivered to rabbit trachea using aerosol dosage form. J. Pharm. Sci. 68(5): 670-671 (1979).
Yusta et al. "GLP-1 receptor activation improves b-cell function and survival following induction of endoplasmic reticulum stress." Cell Metabolism 4:391, 2006.
Zander et al., Effect of 6-week course of glucagon-like peptide 1 on glycaemic control, insulin sensitivity, and beta-cell function in type 2 diabetes: a parallel-group study. Lancet, 359:824-830, 2002.
Crosby, J. Dog Normals, <http://vetmedicine.about.com/od/diseasesconditionsfaqs/tp/TP_dogfacts.htm>, copyright 2013, pp. 1-3.
DedicatedPhase, Preclinical Trials and Research, <http://www.dedicatedphase1.com/preclinical-research.html>, copyright 2006-2011, p. 1.
Heinemann et al., Intra-individual variability of the metabolic effect of inhaled insulin together with an absorption enhancer. Diabetes Care 23(9): 1343-1347 (2000).
McMahon et al., Effects of basal insulin supplementation on disposition of mixed meal in obese patients with NIDDM. Diabetes, vol. 38, pp. 291-303 (1989).
Patton et al., Inhaled insulin. Advanced Drug Delivery Reviews 35, pp. 235-247 (1999).
Zimmermann, K. Respiratory System: Facts, Function, and Diseases, <www.livescience.com/22616-respiratory-system.html> copyright 2013, p. 1.
Heinemann et al., Time-action profile of inhaled insulin. Diabetic Medicine, 14: 63-72 (1997).
American Diabetes Association. "Standards of medical care in diabetes—2009." Diabetes Care. Jan. 2009; 32 Suppl 1: S13-61.
Cefalu et al., Concept, strategies and feasibility of noinvasive insulin delivery. Diabetes Care 27: 239-246 (2004).
Holst et al. "On the effects of glucagon-like peptide-1 on blood glucose regulation in normal and diabetic subjects." Ann N Y Acad Sci. Dec. 26, 1996;805:729-36.
Quattrin et al., Efficacy and Safety of Inhaled Insulin (Exubera) Compared with Subcutaneous Insulin Therapy in Patients with Type 1 Diabetes. Diabetes Care, vol. 27, No. 11, Nov. 2004, p. 2622-2627.
Todd et al. Subcutaneous glucagon-like peptide-1 improves postprandial glycaemic control over a 3-week period in patients with early type 2 diabetes. Clinical Science 95:325, 1998.
Toft-Nielson et al. "Exaggerated secretion of glucagon-like peptide-1 (GLP-1) could cause reactive hypoglycaemia." Diabetologia 41:1180, 1998.
Vilsboll et al. "Reduced postprandial concentrations of intact biologically active glucagon-like peptide-1 in type 2 diabetic patients." Diabetes 50:609, 2001.
Pulmonary Delivery: Innovative Technologies breathing new life into inhalable therapeutics. Ondrug Delivery, Mannkind, pp. 1-24 (2006).

\* cited by examiner

METHODS AND COMPOSITIONS FOR DELIVERING PEPTIDES

CROSS-REFERENCE TO RELATED APPLICATIONS

This application is a continuation of U.S. patent application Ser. No. 12/985,197 filed Jan. 5, 2011, which is a continuation of U.S. patent application Ser. No. 12/635,380 filed Dec. 10, 2009, now U.S. Pat. No. 7,943,178, which is a continuation of U.S. patent application Ser. No. 10/719,734 filed Nov. 21, 2003, now U.S. Pat. No. 7,648,960, which is a continuation of U.S. patent application Ser. No. 10/224,761 filed Aug. 20, 2002, now U.S. Pat. No. 6,652,885, which is a division of U.S. patent application Ser. No. 09/606,468 filed Jun. 29, 2000, now U.S. Pat. No. 6,444,226, which in turn claims the benefit under 35 U.S.C. 119(e) to provisional patent application No. 60/141,433 filed Jun. 29, 1999. Each of these applications and patents are incorporated by reference herein in their entirety.

BACKGROUND OF THE INVENTION

The present invention is generally in the field of pharmaceutical formulations, and more particularly related to methods and compositions for purifying and stabilizing peptides and proteins, such as insulin, which are used in pharmaceutical applications.

In a normal person, the β-cells of the pancreatic islets of Langerhans produce insulin, required by the body for glucose metabolism, in response to an increase in blood glucose concentration. The insulin metabolizes incoming glucose and temporarily stops the liver's conversion of glycogen and lipids to glucose thereby allowing the body to support metabolic activity between meals. The Type I diabetic, however, has a reduced ability or absolute inability to produce insulin due to β-cell destruction and needs to replace the insulin via daily injections or an insulin pump. More common than Type I diabetes, though, is Type II diabetes, which is characterized by insulin resistance and increasingly impaired pancreatic β-cell function. Type II diabetics may still produce insulin, but they may also require insulin replacement therapy.

Type II diabetics typically exhibit a delayed response to increases in blood glucose levels. While normal persons usually release insulin within 2-3 minutes following the consumption of food, Type II diabetics may not secrete endogenous insulin for several hours after consumption. As a result, endogenous glucose production continues after consumption (Pfeiffer, Am. J. Med., 70:579-88 (1981)), and the patient experiences hyperglycemia due to elevated blood glucose levels.

Loss of glucose-induced insulin secretion is one of the earliest disturbances of β-cell function (Cerasi et al., Diabetes, 21:224-34 (1972); Polonsky et al., N. Engl. J. Med., 318:1231-39 (1988)), but the causes and degree of β-cell dysfunction are unknown in most cases. While genetic factors play an important role, (Leahy, Curr. Opin. Endocrinol. Diabetes, 2:300-06 (1995)), some insulin secretory disturbances seem to be acquired and may be at least partially reversible through optimal glucose control. Optimal glucose control via insulin therapy after a meal can lead to a significant improvement in natural glucose-induced insulin release by requiring both normal tissue responsiveness to administered insulin and an abrupt increase in serum insulin concentrations. Therefore, the challenge presented in the treatment of early stage Type II diabetics, those who do not have excessive loss of β-cell function, is to restore the release of insulin following meals.

Most early stage Type II diabetics currently are treated with oral agents, but with little success. Subcutaneous injections of insulin are also rarely effective in providing insulin to Type II diabetics and may actually worsen insulin action because of delayed, variable, and shallow onset of action. It has been shown, however, that if insulin is administered intravenously with a meal, early stage Type II diabetics experience the shutdown of hepatic glucogenesis and exhibit increased physiological glucose control. In addition, their free fatty acids levels fall at a faster rate than without insulin therapy. While possibly effective in treating Type II diabetes, intravenous administration of insulin, is not a reasonable solution, as it is not safe or feasible for patients to intravenously administer insulin at every meal.

Insulin, a polypeptide with a nominal molecular weight of 6,000 Daltons, traditionally has been produced by processing pig and cow pancreas to isolate the natural product. More recently, however, recombinant technology has been used to produce human insulin in vitro. Natural and recombinant human insulin in aqueous solution is in a hexameric configuration, that is, six molecules of recombinant insulin are non-covalently associated in a hexameric complex when dissolved in water in the presence of zinc ions. Hexameric insulin is not rapidly absorbed. In order for recombinant human insulin to be absorbed into a patient's circulation, the hexameric form must first dissociate into dimeric and/or monomeric forms before the material can move into the blood stream. The delay in absorption requires that the recombinant human insulin be administered approximately one half hour prior to meal time in order to produce therapeutic insulin blood level, which can be burdensome to patients who are required to accurately anticipate the times they will be eating. To overcome this delay, analogs of recombinant human insulin, such as HUMALOG™, have been developed, which rapidly disassociate into a virtually entirely monomeric form following subcutaneous administration. Clinical studies have demonstrated that HUMALOG™ is absorbed quantitatively faster than recombinant human insulin after subcutaneous administration. See, for example, U.S. Pat. No. 5,547,929 to Anderson Jr., et al.

In a effort to avoid the disadvantages associated with delivery by injection and to speed absorption, administration of monomeric analogs of insulin via the pulmonary route has been developed. For example, U.S. Pat. No. 5,888,477 to Gonda, et al. discloses having a patient inhale an aerosolized formulation of monomeric insulin to deposit particles of insulin on the patient's lung tissue. However, the monomeric formulation is unstable and rapidly loses activity, while the rate of uptake remains unaltered.

While it would be desirable to produce rapidly absorbable insulin derived from natural sources, transformation of the hexameric form into the monomeric form, such as by removing the zinc from the complex, yields an insulin that is unstable and has an undesirably short shelf life. It therefore would be desirable to provide monomeric forms of insulin, while maintaining its stability in the absence of zinc. It also would be advantageous to provide diabetic patients with monomeric insulin compositions that are suitable for pulmonary administration, provide rapid absorption, and which can be produced in ready-to-use formulations that have a commercially useful shelf-life.

These problems with impurities, metal ions that affect stability or bioavailability, occur with many other proteins and peptides.

U.S. Pat. No. 6,071,497 to Steiner, et al. discloses microparticle drug delivery systems in which the drug is encapsulated in diketopiperazine microparticles which are stable at a pH of 6.4 or less and unstable at pH of greater than 6.4, or which are stable at both acidic and basic pH, but which are unstable at pH between about 6.4 and 8. The patent does not describe monomeric insulin compositions that are suitable for pulmonary administration, provide rapid absorption, and which can be produced in ready-to-use formulations that have a commercially useful shelf-life.

It would therefore be advantageous to develop alternative insulin delivery compositions for Type II diabetics that provide more rapid elevation of insulin blood levels and are easily administered to ensure patient compliance. It also would be desirable to apply the delivery compositions and methods to other biologically active agents.

It is therefore an object of the present invention to provide improved methods for purifying peptides and proteins, especially in the preparation of compositions suitable for pulmonary administration.

It is another object of the present invention to provide stable monomeric peptide compositions suitable for pulmonary delivery.

It is a further object of the present invention to provide methods and compositions for the facilitated transport of insulin and other biologically active agents across biological membranes.

It is another object of the present invention to provide methods and compositions for the improved absorption of insulin or other biologically active agents in the bloodstream.

It is a still further object of the present invention to provide methods and compositions for the improved absorption of insulin or other biologically active agents in the bloodstream characterized by ease of administration.

SUMMARY OF THE INVENTION

Methods are provided for purifying peptides and proteins by incorporating the peptide or protein into a diketopiperazine or competitive complexing agent to facilitate removal one or more impurities, i.e. undesirable components, from the peptide or protein. In a preferred embodiment, a peptide, such as insulin, containing one or more impurities, e.g., zinc ions, is entrapped in diketopiperazine to form a precipitate of peptide/diketopiperazine/impurity, which is then washed with a solvent for the impurity to be removed, which is a nonsolvent for the diketopiperazine and a nonsolvent for the peptide. Alternatively, the impurity can be removed by using complexing agents to selectively complex with and displace the impurities, for example, such as by dialysis.

Formulations and methods also are provided for the improved transport of active agents across biological membranes, resulting, for example, in a rapid increase in blood agent concentration. The formulations include microparticles formed of (i) the active agent, which may be charged or neutral, and (ii) a transport enhancer that masks the charge of the agent and/or that forms hydrogen bonds with the target biological membrane in order to facilitate transport. In a preferred embodiment, insulin is administered via pulmonary delivery of microparticles comprising fumaryl diketopiperazine and insulin in its biologically active form. The charge on the insulin molecule is masked by hydrogen bonding it to the diketopiperazine, thereby enabling the insulin to pass through the target membrane. This method of delivering insulin results in a rapid increase in blood insulin concentration that is comparable to the increase resulting from intravenous delivery.

DETAILED DESCRIPTION OF THE INVENTION

Figure 1A:
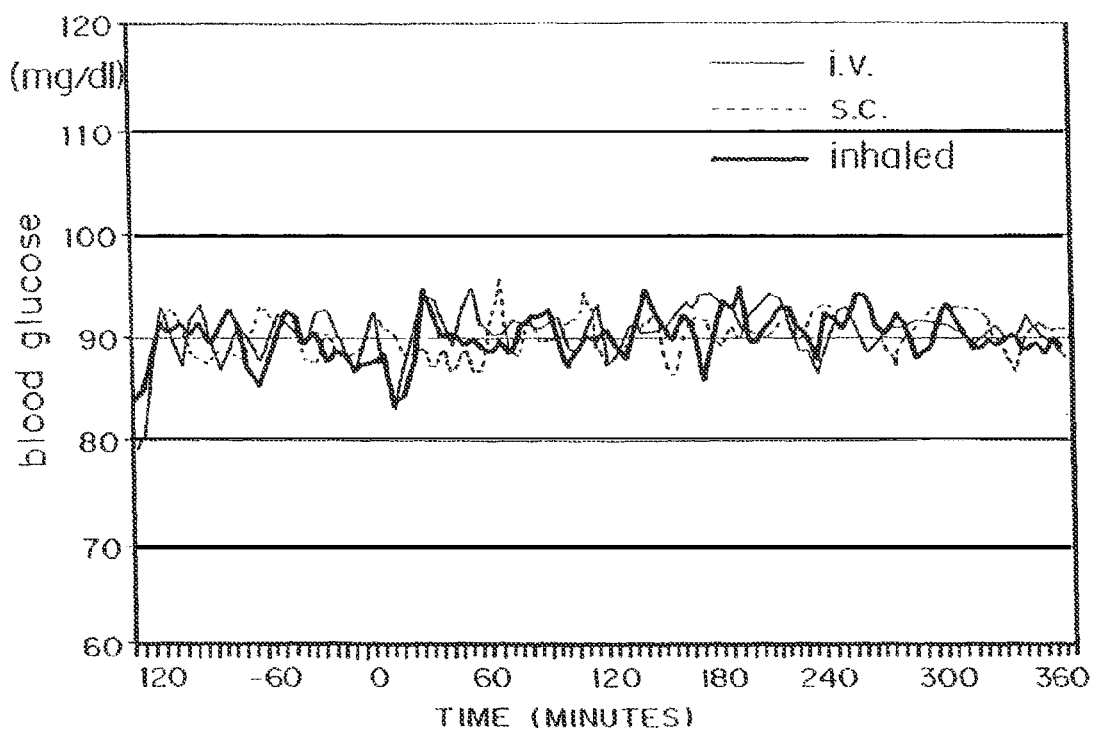
FIG. 1a is a graph of mean blood glucose values over time (minutes).

Encapsulation or entrapment of large polymers, such as proteins and peptides, in diketopiperazines can be used to remove impurities or contaminants such as metal ions or other small molecules. The diketopiperazines also serve both to stabilize and enhance delivery of the entrapped materials. Formulations also have been developed for the enhanced transport of active agents across biological membranes. These formulations include microparticles formed of (i) the active agent, which may be charged or neutral, and (ii) a transport enhancer that masks the charge of the agent and/or that forms hydrogen bonds with the membrane. The formulations can provide rapid increases in the concentration of active agent in the blood following administration of the formulations.

For example, it was discovered that hexameric insulin can be delivered to the lung in fumaryl diketopiperazine formulation, reaching peak blood concentrations within 3-10 minutes. In contrast, insulin administered by the pulmonary route without fumaryl diketopiperazine typically takes between 25-60 minutes to reach peak blood concentrations, while hexameric insulin takes 30-90 minutes to reach peak blood level when administered by subcutaneous injection. This feat has been successfully replicated several times and in several species, including humans.

Removing zinc from insulin typically produces unstable insulin with an undesirably short shelf life. Purification to remove zinc, stabilization and enhanced delivery of insulin is demonstrated by the examples. Formulations of insulin trapped in fumaryl diketopiperazine were found to be stable and have an acceptable shelf life. Measurement of the zinc levels demonstrated that the zinc had been largely removed during the entrapment process, yielding monomeric insulin in a stable delivery formulation.

Rapid absorption of a number of other peptides, including salmon calcitonin, parathyroid hormone 1-34, octreotide, leuprolide and RSV peptide, has been observed when the peptide is pulmonarily delivered in fumaryl diketopiperazine—providing peak blood concentrations within 3-10 minutes after pulmonary delivery.

Materials

A. Agent to be Delivered

The agent to be delivered is referred to herein as the active agent, or molecule to be encapsulated or entrapped. It may or may not be a charged species. Examples of classes of active agents suitable for use in the compositions and methods described herein include therapeutic, prophylactic, and diagnostic agents, as well as dietary supplements, such as vitamins.

The exact mechanism by which the diketopiperazines form a complex with the materials to be delivered is not known, but it is believed that the diketopiperazines form a complex with the material to be purified. This process is referred to herein interchangeably as entrapment or encapsulation.

These materials can be any polymer or large organic molecules, most preferably peptides and proteins. Generally speaking, any form of drug can be entrapped. Examples include synthetic inorganic and organic compounds, proteins and peptides, polysaccharides and other sugars, lipids, and nucleic acid sequences having therapeutic, prophylactic or diagnostic activities. Proteins are defined as consisting of 100 amino acid residues or more; peptide are less than 100 amino acid residues. Unless otherwise stated, the term protein refers to both proteins and peptides. The agents to be incorporated can have a variety of biological activities, such as vasoactive agents, neuroactive agents, hormones, anticoagulants, immunomodulating agents, cytotoxic agents, antibiotics, antivirals, antisense, antigens, and antibodies. In some instances, the proteins may be antibodies or antigens which otherwise would have to be administered by injection to elicit an appropriate response. Representative polymers including proteins, peptides, polysaccharides, nucleic acid molecule, and combinations thereof.

Preferred peptides and proteins include hormones, cytokines and other immunomodulatory peptides, and antigens/vaccines. In a preferred embodiment, the active agent is a monomeric insulin or a stabilized form of insulin which has been purified to remove zinc. In another preferred embodiment, the active agent is glucagon.

The active agent, or drug, can be an antigen, where the molecule is intended to elicit a protective immune response, especially against an agent that preferentially infects the lungs, such as mycoplasma, bacteria causing pneumonia, and respiratory synticial virus. In these cases, it may also be useful to administer the drug in combination with an adjuvant, to increase the immune response to the antigen.

Any genes that would be useful in replacing or supplementing a desired function, or achieving a desired effect such as the inhibition of tumor growth, could be introduced using the matrices described herein. As used herein, a "gene" is an isolated nucleic acid molecule of greater than thirty nucleotides, preferably one hundred nucleotides or more, in length. Examples of genes which replace or supplement function include the genes encoding missing enzymes such as adenosine deaminase (ADA) which has been used in clinical trials to treat ADA deficiency and cofactors such as insulin and coagulation factor VIII. Genes which effect regulation can also be administered, alone or in combination with a gene supplementing or replacing a specific function. For example, a gene encoding a protein which suppresses expression of a particular protein-encoding gene, or vice versa, which induces expresses of a protein-encoding gene, can be administered in the matrix. Examples of genes which are useful in stimulation of the immune response include viral antigens and tumor antigens, as well as cytokines (tumor necrosis factor) and inducers of cytokines (endotoxin), and various pharmacological agents.

Other nucleic acid sequences that can be utilized include antisense molecules which bind to complementary DNA to inhibit transcription, ribozyme molecules, and external guide sequences used to target cleavage by RNAase P.

As used herein, vectors are agents that transport the gene into targeted cells and include a promoter yielding expression of the gene in the cells into which it is delivered. Promoters can be general promoters, yielding expression in a variety of mammalian cells, or cell specific, or even nuclear versus cytoplasmic specific. These are known to those skilled in the art and can be constructed using standard molecular biology protocols. Vectors increasing penetration, such as lipids, liposomes, lipid conjugate forming molecules, surfactants, and other membrane permeability enhancing agents are commercially available and can be delivered with the nucleic acid.

Imaging agents including metals, radioactive isotopes, radioopaque agents, fluorescent dyes, and radiolucent agents also can be incorporated. Examples of radioisotopes and radioopaque agents include gallium, technetium, indium, strontium, iodine, barium, and phosphorus.

Impurities which can be removed from the active agent composition include metal ions such as zinc, and other di- or multi-valent ions, and small inorganic molecules and solvent residuals.

B. Diketopiperazines

Diketopiperazines useful in the present compositions and methods are described, for example, in U.S. Pat. No. 6,071,497, which is incorporated herein in its entirety.

(i). General Formula

The diketopiperazines or their substitution analogs are rigid planar rings with at least six ring atoms containing heteroatoms and unbonded electron pairs. One or both of the nitrogens can be replaced with oxygen to create the substitution analogs diketomorpholine and diketodioxane, respectively. Although it is possible to replace a nitrogen with a sulfur atom, this does not yield a stable structure.

The general formulae for diketopiperazine and its analogs are shown below.

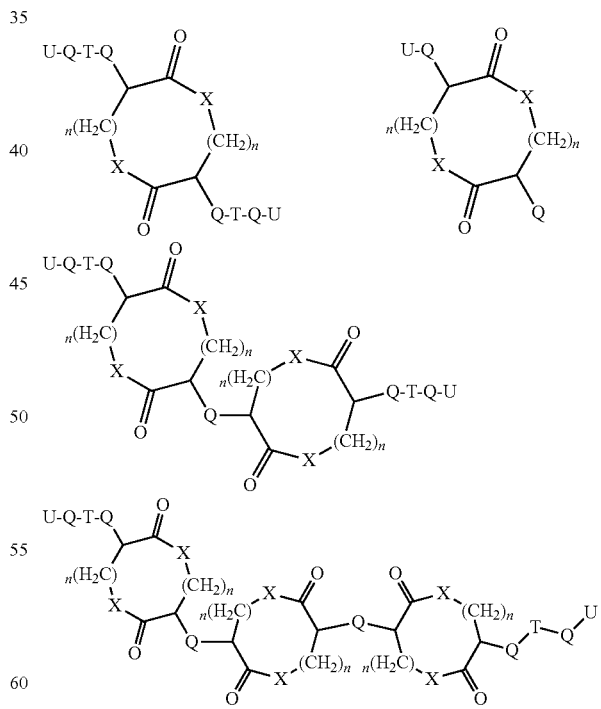

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —C(O), —C(O)NH, —NH, —NQ, —OQO, —O, —NHC(O), —OP(O), —P(O)O, —OP $(O)_2$, $—P(O)_2O$, $—OS(O)_2$, or $—S(O)_3$; U is an acid group, such as a carboxylic acid, phosphoric acid, phosphonic acid and sulfonic acid, or a basic group, such as primary, secondary and tertiary amines, quaternary ammonium salts, guanidine, aniline, heterocyclic derivatives, such as pyridine and morpholine, or a zwitterionic $C_{1-20}$ chain containing at least one acidic group and at least one basic group, for example, those described above, wherein the side chains can be further functionalized with an alkene or alkyne group at any position, one or more of the carbons on the side chain can be replaced with an oxygen, for example, to provide short polyethylene glycol chains, one or more of the carbons can be functionalized with an acidic or basic group, as described above, and wherein the ring atoms X at positions 1 and 4 are either O or N.

As used herein, "side chains" are defined as Q-T-Q-U or Q-U, wherein Q, T, and U are defined above.

Examples of acidic side chains include, but are not limited, to cis and trans $—CH=CH—CO_2H$, $—CH(CH_3)=CH(CH_3)—CO_2H$, $—(CH_2)_3—CO_2H$, $—CH_2CH(CH_3)—CO_2H$, $—CH(CH_2CO_2H)=CH_2$, -(tetrafluoro)benzoic acid, -benzoic acid and $—CH(NHC(O)CF_3)—CH_2—CO_2H$.

Examples of basic side chains include, but are not limited to, -aniline, -phenyl-C(NH)NH_2, -phenyl-C(NH)NH(alkyl), -phenyl-C(NH)N(alkyl)_2 and $—(CH_2)_4NHC(O)CH(NH_2)CH(NH_2)CO_2H$.

Examples of zwitterionic side chains include, but are not limited to, $—CH(NH_2)—CH_2—CO_2H$ and $—NH(CH_2)_{1-20}CO_2H$.

The term aralkyl refers to an aryl group with an alkyl substituent.

The term heterocyclic-alkyl refers to a heterocyclic group with an alkyl substituent.

The term alkaryl refers to an alkyl group that has an aryl substituent.

The term alkyl-heterocyclic refers to an alkyl group that has a heterocyclic substituent.

The term alkene, as referred to herein, and unless otherwise specified, refers to an alkene group of $C_2$ to $C_{10}$, and specifically includes vinyl and allyl.

The term alkyne, as referred to herein, and unless otherwise specified, refers to an alkyne group of $C_2$ to $C_{10}$. As used herein, "diketopiperazines" includes diketopiperazines and derivatives and modifications thereof falling within the scope of the above-general formula.

Fumaryl diketopiperazine is most preferred for pulmonary applications.

(ii). Synthesis

Diketopiperazines can be formed by cyclodimerization of amino acid ester derivatives, as described by Katchalski, et al., J. Amer. Chem. Soc. 68:879-80 (1946), by cyclization of dipeptide ester derivatives, or by thermal dehydration of amino acid derivatives in high-boiling solvents, as described by Kopple, et al., J. Org. Chem. 32(2):862-64 (1968), the teachings of which are incorporated herein. 2,5-diketo-3,6-di(aminobutyl)piperazine (Katchalski et al. refer to this as lysine anhydride) was prepared via cyclodimerization of N-epsilon-P-L-lysine in molten phenol, similar to the Kopple method in J. Org. Chem., followed by removal of the blocking (P)-groups with 4.3 M HBr in acetic acid. This route is preferred because it uses a commercially available starting material, it involves reaction conditions that are reported to preserve stereochemistry of the starting materials in the product and all steps can be easily scaled up for manufacture.

Diketomorpholine and diketooxetane derivatives can be prepared by stepwise cyclization in a manner similar to that disclosed in Katchalski, et al., J. Amer. Chem. Soc. 68:879-80 (1946).

Diketopiperazines can be radiolabelled. Means for attaching radiolabels are known to those skilled in the art. Radiolabelled diketopiperazines can be prepared, for example, by reacting tritium gas with those compounds listed above that contain a double or triple bond. A carbon-14 radiolabelled carbon can be incorporated into the side chain by using $^{14}C$ labeled precursors which are readily available. These radiolabelled diketopiperazines can be detected in vivo after the resulting microparticles are administered to a subject.

(a) Synthesis of Symmetrical Diketopiperazine Derivatives

The diketopiperazine derivatives are symmetrical when both side chains are identical. The side chains can contain acidic groups, basic groups, or combinations thereof.

One example of a symmetrical diketopiperazine derivative is 2,5-diketo-3,6-di(4-succinylaminobutyl)piperazine. 2,5-diketo-3,6-di(aminobutyl)piperazine is exhaustively succinylated with succinic anhydride in mildly alkaline aqueous solution to yield a product which is readily soluble in weakly alkaline aqueous solution, but which is quite insoluble in acidic aqueous solutions. When concentrated solutions of the compound in weakly alkaline media are rapidly acidified under appropriate conditions, the material separates from the solution as microparticles.

Other preferred compounds can be obtained by replacing the succinyl group(s) in the above compound with glutaryl, maleyl or fumaryl groups.

(b) Synthesis of Asymmetrical Diketopiperazine Derivatives

One method for preparing unsymmetrical diketopiperazine derivatives is to protect functional groups on the side chain, selectively deprotect one of the side chains, react the deprotected functional group to form a first side chain, deprotect the second functional group, and react the deprotected functional group to form a second side chain.

Diketopiperazine derivatives with protected acidic side chains, such as cyclo-Lys(P)Lys(P), wherein P is a benzyloxycarbonyl group, or other protecting group known to those skilled in the art, can be selectively deprotected. The protecting groups can be selectively cleaved by using limiting reagents, such as HBr in the case of the benzyloxycarbonyl group, or fluoride ion in the case of silicon protecting groups, and by using controlled time intervals. In this manner, reaction mixtures which contain unprotected, monoprotected and di-protected diketopiperazine derivatives can be obtained. These compounds have different solubilities in various solvents and pH ranges, and can be separated by selective precipitation and removal. An appropriate solvent, for example, ether, can then be added to such reaction mixtures to precipitate all of these materials together. This can stop the deprotection reaction before completion by removing the diketopiperazines from the reactants used to deprotect the protecting groups. By stirring the mixed precipitate with water, both the partially and completely reacted species can be dissolved as salts in the aqueous medium. The unreacted starting material can be removed by centrifugation or filtration. By adjusting the pH of the aqueous solution to a weakly alkaline condition, the asymmetric monoprotected product containing a single protecting group precipitates from the solution, leaving the completely deprotected material in solution.

In the case of diketopiperazine derivatives with basic side chains, the basic groups can also be selectively deprotected.

As described above, the deprotection step can be stopped before completion, for example, by adding a suitable solvent to the reaction. By carefully adjusting the solution pH, the deprotected derivative can be removed by filtration, leaving the partially and totally deprotected derivatives in solution. By adjusting the pH of the solution to a slightly acidic condition, the monoprotected derivative precipitates out of solution and can be isolated.

Zwitterionic diketopiperazine derivatives can also be selectively deprotected, as described above. In the last step, adjusting the pH to a slightly acidic condition precipitates the monoprotected compound with a free acidic group. Adjusting the pH to a slightly basic condition precipitates the monoprotected compound with a free basic group.

Limited removal of protecting groups by other mechanisms, including but not limited to cleaving protecting groups that are cleaved by hydrogenation by using a limited amount of hydrogen gas in the presence of palladium catalysts. The resulting product is also an asymmetric partially deprotected diketopiperazine derivative. These derivatives can be isolated essentially as described above.

The monoprotected diketopiperazine is reacted to produce a diketopiperazine with one sidechain and protecting group. Removal of protecting groups and coupling with other side chains yields unsymmetrically substituted diketopiperazines with a mix of acidic, basic, and zwitterionic sidechains.

Other materials that exhibit this response to pH can be obtained by functionalizing the amide ring nitrogens of the diketopiperazine ring.

C. Transport Enhancers

In a preferred embodiment, the active agent is complexed with a transport enhancer which is degradable and capable of forming hydrogen bonds with the target biological membrane in order to facilitate transport of the agent across the membrane. The transport enhancer also is capable of forming hydrogen bonds with the active agent, if charged, in order to mask the charge and facilitate transport of the agent across the membrane. A preferred transport enhancer is diketopiperazine.

The transport enhancer preferably is biodegradable and may provide linear, pulsed or bulk release of the active agent. The transport enhancer may be a natural or synthetic polymer and may be modified through substitutions or additions of chemical groups, including alkyly, alkylene, hydroxylations, oxidations, and other modifications routinely made by those skilled in the art.

A preferred transport enhancer is fumaryl diketopiperazine. Other diketopiperazines which may be useful as a transport enhancer are described above.

Like most proteins and peptides, insulin is a charged molecule, which impedes its ability to cross charged biological membranes. It has been found that when insulin hydrogen bonds to fumaryl diketopiperazine, the charge of the peptide is masked, thereby facilitating or enhancing the passage of insulin across the membranes, such as mucosal membranes, and into the blood.

II. Methods

A. Encapsulation

In one embodiment, active agent is encapsulated within microparticles by dissolving a diketopiperazine with acidic side chains in bicarbonate or other basic solution, adding the active agent in solution or suspension, and then precipitating the microparticle by adding acid, such as 1 M citric acid.

In another embodiment, active agent is encapsulated within microparticles by dissolving a diketopiperazine with basic side chains in an acidic solution, such as 1 M citric acid, adding the active agent in solution or suspension, and then precipitating the microparticle by adding bicarbonate or another basic solution.

In still another embodiment, active agent is encapsulated within microparticles by dissolving a diketopiperazine with both acidic and basic side chains in an acidic or basic solution, adding the active agent in solution or suspension to be encapsulated, then precipitating the microparticle by neutralizing the solution.

The microparticles can be stored in the dried state and suspended for administration to a patient. In the first embodiment, the reconstituted microparticles maintain their stability in an acidic medium and dissociate as the medium approaches physiological pH in the range of between 6 and 14. In the second embodiment, suspended microparticles maintain their stability in a basic medium and dissociate at a pH of between 0 and 6. In the third embodiment, the reconstituted microparticles maintain their stability in an acidic or basic medium and dissociate as the medium approaches physiological pH in the range of pH between 6 and 8.

The impurities typically are removed when the microparticles are precipitated. However, impurities also can be removed by washing the particles to dissolve the impurities. A preferred wash solution is water or an aqueous buffer. Solvents other than water also can be used to wash the microspheres or precipitate the diketopiperazines, in order to remove impurities that are not water soluble. Any solvent in which neither the cargo nor the fumaryl diketopiperazine is soluble are suitable. Examples include acetic acid, ethanol, and toluene.

In an alternative embodiment, microparticles of diketopiperazine are prepared and provided in a suspension, typically an aqueous suspension, to which a solution of the active agent then is added. The suspension is then lyophilized or freeze dried to yield diketopiperazine microparticles having a coating of active agent. In a preferred embodiment, the active agent is insulin in a hexameric form. Zinc ions can then be removed by washing the microparticles with an appropriate solvent.

As used herein, the term "entrapped" with reference to an active agent in/with a diketopiperazine includes coating of the active agent onto microparticles of the diketopiperazine.

The diketopiperazine microparticles have been found to have a higher affinity for insulin than does zinc. Insulin has been found to be stabilized within an ordered lattice array of fumaryl diketopiperazine. In this state, in the sufficient absence of zinc ions, the insulin is predominately dimeric and monomeric, as opposed to it hexameric state. The insulin therefore more readily dissociates to its monomeric state, which is the state in which insulin exerts its biological activity.

Other complexing agents may be substituted for the diketopiperazine. Other representative complexing agents include serum albumin and other proteins, alginic acid, antibodies, cyclodextrins, phospholipids, and lecithin. For example, insulin contaminated with zinc can be complexed with bovine serum albumin. The complex can be dialyzed in tubing with a molecular weight cut-off below 1,000 Daltons to separate and remove the zinc. Once sufficient amounts of zinc have been dialyzed away, as evidenced by its presence in the dialysate, the dispersion is transferred to dialysis tubing with a molecular weight cut-off below 10,000 Daltons. Only monomeric insulin will pass through the tubing into the dialysate, leaving any remaining hexameric zinc complexed insulin behind. The purified insulin can be captured from the dialysate.

These materials may not, however, provide sufficient stabilization of unstable or labile drugs.

B. Administration

The compositions of active agent described herein can be administered to patients in need of the active agent. The compositions preferably are administered in the form of microparticles, which can be in a dry powder form for pulmonary administration or suspended in an appropriate pharmaceutical carrier, such as saline.

The microparticles preferably are stored in dry or lyophilized form until immediately before administration. The microparticles then can be administered directly as a dry powder, such as by inhalation using, for example, dry powder inhalers known in the art. Alternatively, the microparticles can be suspended in a sufficient volume of pharmaceutical carrier, for example, as an aqueous solution for administration as an aerosol.

The microparticles also can be administered via oral, subcutaneous, and intravenous routes.

The compositions can be administered to any targeted biological membrane, preferably a mucosal membrane of a patient. In a preferred embodiment, the patient is a human suffering from Type II diabetes. In a preferred embodiment, the composition delivers insulin in biologically active form to the patient, which provides a spike of serum insulin concentration which simulates the normal response to eating.

In a preferred embodiment, hexameric insulin is entrapped in fumaryl diketopiperazine to form a solid precipitate of monomeric insulin in the fumaryl diketopiperazine, which then is washed with aqueous solution to remove the free zinc. This formulation demonstrates blood uptake following pulmonary administration at a rate 2.5 times the rate of insulin uptake following subcutaneous injection, with peak blood levels occurring at between 7.5 and 10 minutes after administration.

The range of loading of the drug to be delivered is typically between about 0.01% and 90%, depending on the form and size of the drug to be delivered and the target tissue. In a preferred embodiment using diketopiperazines, the preferred range is from 0.1% to 50% loading by weight of drug. The appropriate dosage can be determined, for example, by the amount of incorporated/encapsulated agent, the rate of its release from the microparticles, and, in a preferred embodiment, the patient's blood glucose level.

One preferred application is in the treatment of hyperinsulinemia. In a preferred embodiment, microparticles of the composition wherein the active agent is glucagon can be administered by continuous subcutaneous infusion. Glucagon is an extremely unstable peptide, but can be stabilized in particles of diketopiperazine, for example. The stabilized glucagon/diketopiperazine microparticles can be made by adding glucagon to a solution of diketopiperazine which hydrogen bonds to the glucagon and when the solution is acidified, such as by adding a food acid, both the diketopiperazine and the glucagon self-assemble to form uniform microspheres having a mean particle size of, for example, about 2 μm. In this process, approximately 95% of the glucagon is pulled out of solution and is evenly distributed within the diketopiperazine microparticle. These particles can readily be suspended and infused subcutaneously with a standard infusion pump. Then the glucagon/diketopiperazine particles are contacted with the near neutral pH environment of the subcutaneous fluid, where they dissolve, thereby releasing glucagon in its pharmacologically active state.

The compositions and methods described herein are further described by the following non-limiting examples.

Example 1

Removal of Zinc from U.S.P. Injectable Insulin

Insulin trapped in fumaryl diketopiperazine was analyzed to assess whether zinc was removed during the entrapment process. The insulin used as the starting material met U.S.P. standards for injectable insulin, and according to the certificate of analysis, the insulin contained a considerable quantity of zinc: 0.41%. This insulin was then entrapped in fumaryl diketopiperazine to form a solid fumaryl diketopiperazine/insulin mixture, as described above.

Following entrapment of the insulin in fumaryl diketopiperazine, the amount of zinc theoretically should be present in the same proportion as it existed in the neat insulin. Using the certificate of analysis value, it was calculated that one should expect to find 697 parts per million (ppm) of zinc per gram in the solid yield of fumaryl diketopiperazine/insulin. Surprisingly, the quantity of zinc present the solid fumaryl diketopiperazine/insulin was measured to be only 6 ppm. The "missing" zinc was presumably eliminated with the water used to wash the insulin/fumaryl diketopiperazine precipitate.

Example 2

Bioavailability of Insulin in Diketopiperazine Pulmonary Formulation

Subjects and Methods

The study was reviewed and approved by the ethical review committee of the Heinrich-Heine-University, Dusseldorf, and conducted according to local regulations, the Declaration of Helsinki and the rules of Good Clinical Practice.

The study was conducted with 5 healthy male volunteers. Inclusion criteria were good health, as judged by physical examination, age: 18 to 40 years, body mass index: 18 to 26 kg/m$^2$, capability to reach peak inspiratory flow of ≥4 l/sec measured by a computer assisted spirometry and a $FEV_1$ equal to or greater than 80% of predicted normal ($FEV_1$=forced expiratory volume in one second). Exclusion criteria were Diabetes mellitus type 1 or 2, prevalence of human insulin antibodies, history of hypersensitivity to the study medication or to drugs with similar chemical structures, history or severe or multiple allergies, treatment with any other investigational drug in the last 3 months before study entry, progressive fatal disease, history of drug or alcohol abuse, current drug therapy with other drugs, history significant cardiovascular, respiratory, gastrointestinal, hepatic, renal, neurological, psychiatric and/or hematological disease, ongoing respiratory tract infection or subjects defined as being smokers with evidence or history of tobacco or nicotine use.

Conduct of the Study

On the morning of the study days, the subjects came to the hospital (fasting, except for water, from midnight onward) at 7:30 a.m. The subjects were restricted from excessive physical activities and an intake of alcohol for 24 hours before each treatment day. They were randomly assigned to one of the three treatment arms. The subjects received a constant intravenous regular human insulin infusion, which was kept at 0.15 mU $min^{-1}$ $kg^{-1}$ so that serum insulin concentrations were established at 10-15 μU/ml during a period of 2 hours before time point 0. This low-dose infusion was continued throughout the test to suppress endogenous insulin secretion. Blood glucose was kept constant at a level of 90 mg/dl throughout the glucose clamp by a glucose controlled infusion system (BIOSTATOR™). The glucose clamp algorithm was based on the actual measured blood glucose concentration and the grade of variability in the minutes before to calculate the glucose infusion rates for keeping the blood glucose concentration constant. The insulin application (5 U i.v. or 10 U s.c. injection or three deep breaths inhalation per capsule (2 capsules with 50 U each) applied with a commercial inhalation device (Boehringer Ingelheim)) had to be finished immediately before time point 0. The duration of the clamp experiment was 6 hours from time point 0. Glucose infusion rates, blood glucose, serum-insulin and C-peptide were measured.

Bioefficacy and Bioavailability

To determine bioefficacy, the areas under the curve of the glucose infusion rates were calculated for the first 3 hours ($AUC_{0-180}$) after the administration and for the overall observation period of six hours after the administration ($AUC_{0-360}$) and were correlated to the amount of insulin applied. To determine bioavailability, the areas under the curve of the insulin concentrations were calculated for the first 3 hours ($AUC_{0-180}$) after the administration and for the overall observation period of six hours after the administration ($AUC_{0-360}$) and correlated to the amount of insulin applied.

In this clamp study, inhalation of 100 U of TECHNOSPHERE™/Insulin was well tolerated and was demonstrated to have a substantial blood glucose lowering effect with a relative bioavailability of 25.8% for the first three hours as calculated from the achieved serum insulin concentrations. TECHNOSPHERES™ are microparticles (also referred to herein as microspheres) formed of diketopiperazine that of self-assembles into an ordered lattice array at particular pHs, typically a low pH. They typically are produced to have a mean diameter between about 1 and about 5 μm.

Results

Figure 1B:
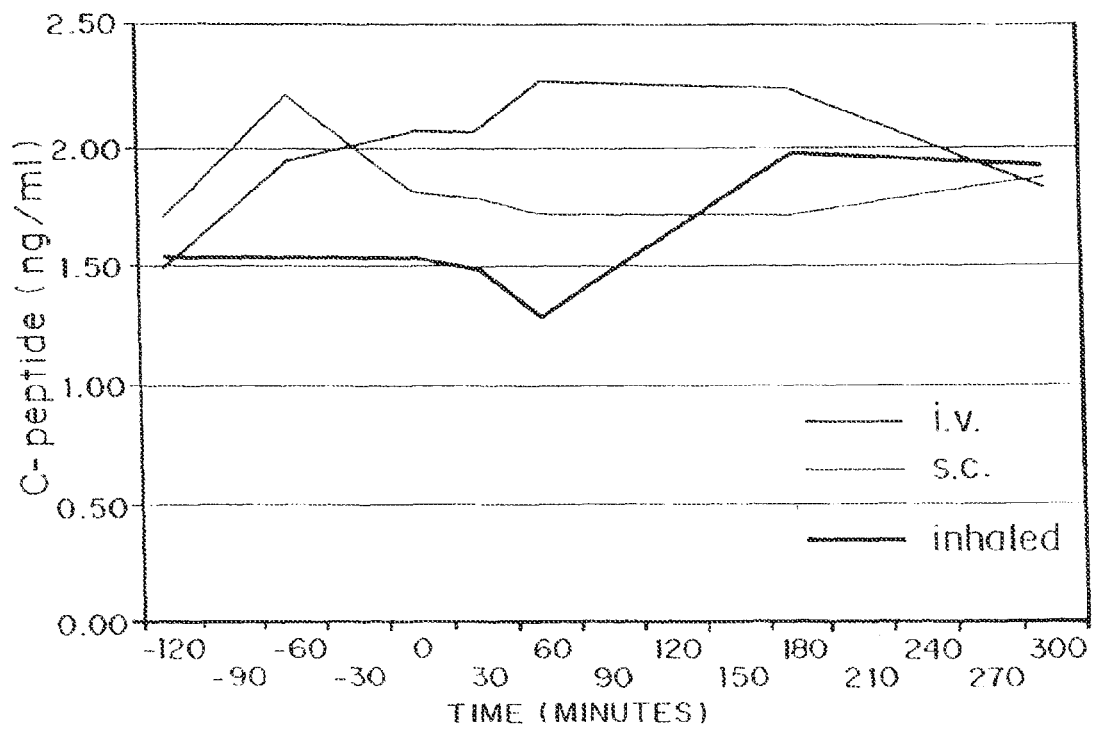
FIG. 1b is a graph of mean C-peptide concentrations during experiments comparing levels of C-peptide (ng/ml) over time (minutes) when insulin was administered intravenously, subcutaneously, and by inhalation.
Figure 2A:
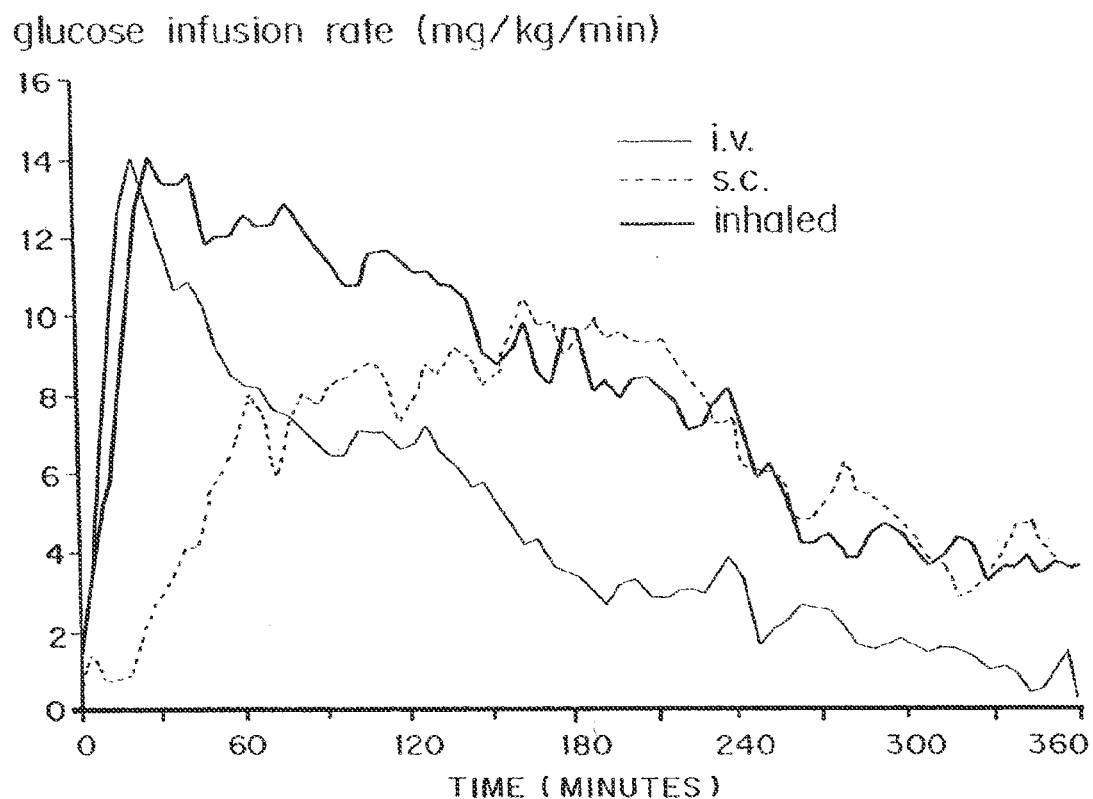
FIG. 2a is a graph of glucose infusion rate (mg/kg/min) over time (minutes) comparing insulin administered intravenously, subcutaneously, and by inhalation.
Figure 2B:
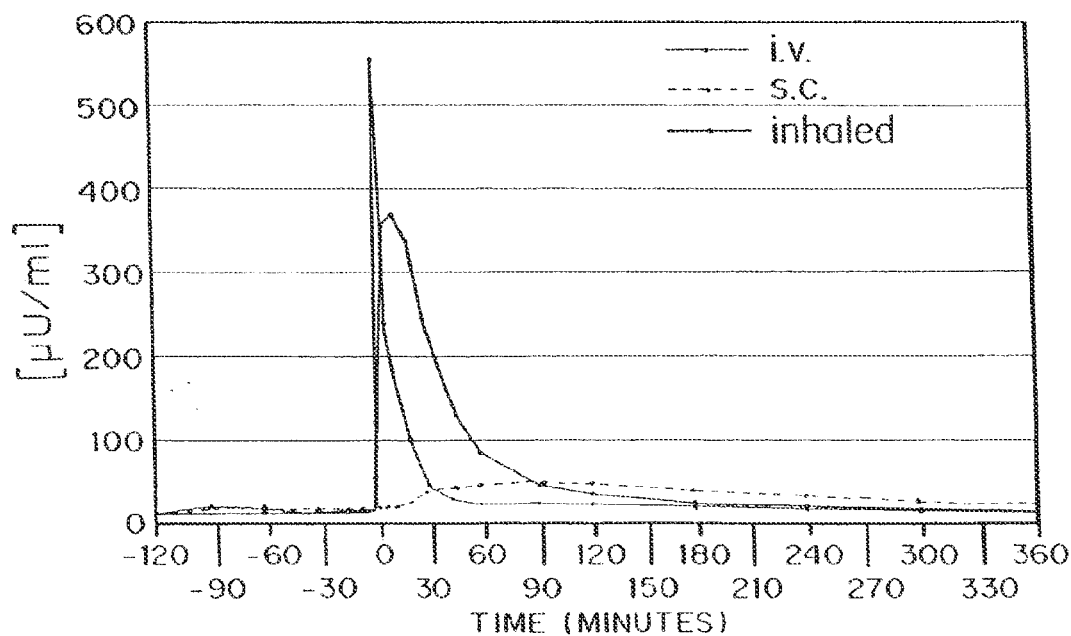
FIG. 2b is a graph of mean insulin concentrations ($\mu$U/ml) over time (minutes) comparing insulin administered intravenously, subcutaneously, and by inhalation.

The pharmacokinetic results are illustrated in FIGS. 1 and 2 and in Table 1.

Efficacy Results

Inhalation of 100 U of TECHNOSPHERE™/Insulin (inhalation of 100 U) revealed a peak of insulin concentration after 13 min (intravenous (i.v.) (5 U): 5 min, subcutaneous (s.c.) (10 U): 121 min) and a return of the insulin levels to baseline after 180 min (i.v.: 60 min, s.c. 360 min). Biological action as measured by glucose infusion rate peaked after 39 min (i.v. 14 min, s.c.: 163 min) and lasted for more than 360 min (i.v.: 240 min, s.c.: >360 min). Absolute bioavailability (comparison to i.v. application) was 14.6±5.1% for the first 3 hours and 15.5±5.6% for the first 6 hours. Relative bioavailability (comparison to s.c. application) was 25.8±11.7% for the first 3 hours and 16.4±7.9% for the first 6 hours.

TABLE 1

Pharmacokinetic Parameters

| | Intravenous Administration | Inhaled | Subcutaneous Administration |
|---|---|---|---|
| Parameter Calculated on Glucose Infusion Rate | | | |
| T50%* | 9 min | 13 min | 60 min |
| Tmax | 14 min | 39 min | 163 min |
| T-50%** | 82 min | 240 min | 240 min |
| T to baseline | 240 min | >360 min | >360 min |
| Parameter Calculated on Insulin Levels | | | |
| T50%* | 2 min | 2.5 min | 27 min |
| Tmax | 5 min | 13 min | 121 min |
| T-50%** | 6 min | 35 min | 250 min |
| T to baseline | 60 min | 180 min | 360 min |

*time from baseline to half-maximal values
**time from baseline to half-maximal after passing Tmax Safety Results TECHNOSPHERE™/Insulin was shown to be safe in all patients. One patient was coughing during the inhalation without any further symptoms or signs of deterioration of the breathing system.

Conclusions

Inhalation of 100 U of TECHNOSPHERE™/Insulin was well tolerated and was demonstrated to have a substantial blood glucose lowering effect with a relative bioavailability of 25.8% for the first 3 hours as calculated from the achieved serum insulin concentrations.

Summary

In this study, the inhalation of TECHNOSPHERE™/Insulin (the formulation of example 1) was demonstrated in healthy human subjects to have a time-action profile with a rapid peak of insulin concentration (Tmax: 13 min) and rapid onset of action (Tmax: 39 min) and a sustained action over more than 6 hours. The total metabolic effect measured after inhalation of 100 U of TECHNOSPHERE™/Insulin was larger than after subcutaneous injection of 10 U of insulin. The relative bioefficacy of TECHNOSPHERE™/Insulin was calculated to be 19.0%, while the relative bioavailability was determined to be 25.8% in the first three hours.

The data also show that inhalation of TECHNOSPHERE™/Insulin resulted in a much more rapid onset of action than s.c. insulin injection that was close to the onset of action of i.v. insulin injection, while duration of action of TECHNOSPHERE™/Insulin was comparable to that of s.c. insulin injection.

The drug was well tolerated and no serious adverse events were reported during the entire trial.

Example 3

Removal of Impurity from Proprietary Peptide

A proprietary peptide containing an impurity was trapped in fumaryl diketopiperazine, forming a peptide/fumaryl diketopiperazine precipitate. The precipitate was washed with water to remove the impurity. The peptide is rather unstable and trapping it in fumaryl diketopiperazine markedly improves its stability; both as a dry powder and in aqueous suspension for injection.

Example 4

Stabilized Glucagon Formulations

Formulation

Glucagon was formulated under sterile conditions, into a stabilized complex by precipitation in acidic solution with fumaryl diketopiperazine (3,6bis[N-fumaryl-N-(n-butyl) amino]-2,5-diketopiperazine). The complex was washed and lyophilized, yielding a sterile dry powder formulation of diketopiperazine/glucagon (hereinafter referred to as "TG") containing from 1.2 to 8.2% glucagon by weight, depending upon the formulation parameters desired (allowing physicians to increase dose yet keep the volume constant). The TG powder was suspended in an appropriate media suitable for subcutaneous delivery in a MiniMed 507C infusion pump.

Stability Protocol

Glucagon and TG were suspended in infusion media and incubated at 40.degree. C. in a water bath for varying amounts of time up to 150 hours.

Glucagon HPLC Analysis

An adaptation of USP method for glucagon analysis was employed. A Waters Symmetry Shield RP8 column (5 µm, 3.9×150 mm) and guard RP8 column (5 µm, 3.9×20 mm) were used at a flow rate of 1 mL/min. and a detection wavelength of 214 nm. The gradient method consisted of mobile phase A: 9.8 g $NaH_2PO_4$ (0.0816 M) and 170 mg L-cysteine (1.4 mM) per liter HPLC grade water, adjusted pH to 2.6 with phosphoric acid; and B: acetonitrile. Glucagon solutions were diluted as needed with water and injected. TG samples were prepared by adding {fraction (1/10)}$^{th}$ volume 1 M Tris pH 10.0 to sample to solubilize the fumaryl diketopiperazine.

Rat Study Protocol

Sprague Dawley rats 200-250 g were fasted overnight and given subcutaneous injection of glucagon or TG (0.75 mg/kg) in an appropriate media that had been held at 25° C. for 0, 24, or 48 hours. Blood samples were taken at −10, −5, 0, 5, 10, 15, 20, 30, 45, and 60 minutes post dose and analyzed for blood glucose (HemCue B-glucose analyzer, Hemocue AB, Angelholm Sweden). Mean baseline was determined (pre-dose measurements) and was subtracted from the subsequent data and plotted vs. time. This was done to assure that the TG formulation, which appeared to not degrade significantly, showed appropriate pharmacological activity.

Results

Following 40° C. incubation, HPLC analysis showed an increase in breakdown products in the glucagon preparation. By contrast, TG has only one minor degradation peak (RT=6) which correlated with the slightly less active oxidative form of glucagon. Glucagon without diketopiperazine (i.e. without TECHNOSPHERES™) had many degradation peaks, some of which contributed to an enhanced effect and others that reduced the potency of glucagon.

The TG sterile lyophilized powder was shipped frozen to a hospital, where it was re-suspended in sterile media. The material re-suspended well and each vial was continuously infused over a 72 hour period.

Conclusion

Standard preparations of glucagon are not suitable for regulation of blood glucose by continuous subcutaneous infusion. Administration of such preparations containing variable amounts of the deamidated and hydrolysed forms resulted in highly variable blood glucose levels. Suspensions of TECHNOSPHERES™/glucagon, which is stabilized, does not aggregate and contains clinically irrelevant amounts of breakdown products. As such TG can be and has been used as a therapy for hyperinsulinemia, providing consistent, elevated glucose levels when administered subcutaneously over time.

Modifications and variations of the present invention will be obvious to those of skill in the art from the foregoing detailed description. Such modifications and variations are intended to come within the scope of the following claims.

What is claimed is:

1. A method of delivering insulin to a human comprising administering a composition comprising insulin bound to a complexing agent to said human by pulmonary inhalation, wherein the composition delivers insulin to the patient in biologically active form after inhalation, wherein said composition produces a rapid onset of insulin action wherein (a) peak blood insulin levels ($Tmax_{[INS]}$) are achieved about 13 minutes after inhalation, or (b) peak biological action, measurable as glucose infusion rate ($Tmax_{GIR}$) is achieved about 39 minutes after inhalation.

2. The method of claim 1 wherein ($Tmax_{[INS]}$) is achieved about 13 minutes after inhalation.

3. The method of claim 1 wherein peak biological action, measurable as ($Tmax_{GIR}$), is achieved about 39 minutes after inhalation.

4. The method of claim 1 wherein the complexing agent is a diketopiperazine derivative.

5. The method of claim 4 wherein the diketopiperazine derivative has the formula 2,5-diketo-3,6-di(4-X-aminobutyl)piperazine, wherein X is selected from the group consisting of fumaryl, succinyl, maleyl, and glutaryl.

6. The method of claim 5 wherein the diketopiperazine derivative is 2,5-diketo-3,6-di(4-fumaryl-aminobutyl)piperazine.

7. The method of claim 1 wherein the composition is provided as a dry powder.

8. A composition comprising insulin bound to a complexing agent wherein the composition is-prepared by a method comprising:

formulating a composition for pulmonary inhalation;

wherein the composition delivers insulin to the patient in biologically active form after inhalation, wherein said composition produces a rapid onset of insulin action when administered to a human wherein (a) peak blood insulin levels ($Tmax_{[INS]}$) are achieved about 13 minutes after inhalation, or (b) peak biological action, measurable as glucose infusion rate ($Tmax_{GIR}$), is achieved about 39 minutes after inhalation.

9. The composition of claim 8 wherein ($Tmax_{[INS]}$) is achieved about 13 minutes after inhalation.

10. The composition of claim 8 wherein peak biological action, measurable as ($Tmax_{GIR}$), is achieved about 39 minutes after inhalation.

11. The composition of claim 8 wherein the complexing agent is a diketopiperazine derivative.

12. The composition of claim 11 wherein the diketopiperazine derivative has the formula 2,5-diketo-3,6-di(4-X-aminobutyl)piperazine, wherein X is selected from the group consisting of fumaryl, succinyl, maleyl, and glutaryl.

13. The composition of claim 12 wherein the diketopiperazine derivative is 2,5-diketo-3,6-di(4-fumaryl-aminobutyl)piperazine.

14. The composition of claim 8 wherein the composition is provided as a dry powder.

* * * * *